United States Patent
Braeckmans et al.

(10) Patent No.: US 12,091,655 B2
(45) Date of Patent: Sep. 17, 2024

(54) METHOD TO SELECTIVELY PERMEABILIZE AND/OR FRAGMENTIZE CELLS

(71) Applicant: UNIVERSITEIT GENT, Ghent (BE)

(72) Inventors: Kevin Braeckmans, Lokeren (BE); Stefaan De Smedt, Mariakerke (BE); Félix Sauvage, Roubaix (FR); Aranit Harizaj, Ghent (BE); Ranhua Xiong, Jiangsu (CN)

(73) Assignee: Universiteit Gent, Ghent (BE)

( * ) Notice: Subject to any disclaimer, the term of this patent is extended or adjusted under 35 U.S.C. 154(b) by 0 days.

(21) Appl. No.: 18/551,165

(22) PCT Filed: Mar. 22, 2022

(86) PCT No.: PCT/EP2022/057464
§ 371 (c)(1),
(2) Date: Sep. 18, 2023

(87) PCT Pub. No.: WO2022/200333
PCT Pub. Date: Sep. 29, 2022

(65) Prior Publication Data
US 2024/0175003 A1    May 30, 2024

(30) Foreign Application Priority Data
Mar. 23, 2021    (EP) .................... 21164292

(51) Int. Cl.
*C12N 13/00* (2006.01)
*A61F 9/008* (2006.01)

(52) U.S. Cl.
CPC .......... *C12N 13/00* (2013.01); *A61F 9/00802* (2013.01); *A61F 2009/00872* (2013.01); *A61F 2009/00885* (2013.01)

(58) Field of Classification Search
None
See application file for complete search history.

(56) References Cited

FOREIGN PATENT DOCUMENTS

| WO | 2006078987 A2 | 7/2006 |
|---|---|---|
| WO | 2009017695 A1 | 2/2009 |
| WO | 2142158631 A2 | 11/2012 |

OTHER PUBLICATIONS

Lopez-Lopez et al. "Photodynamic Inactivation of *Staphlococcus aureus* Biofilms Using a Hexanuclear Molybdenum Compex Embedded in Transparent polyHEMA Hydrogels" (2020), ACS Biomater Sci Eng, vol. 6: 6995-7003. (Year: 2020).*
International Search Report for International Application No. PCT/EP2022/057464, mailed Jun. 22, 2022, 4 pages.
International Written Opinion for International Application No. PCT/EP2022/057464, mailed Jun. 22, 2022, 6 pages.
Lapotko D et al, "Method of laser activated nano-thermolysis for elimination of tumor cells", Jul. 28, 2006 (Jul. 28, 2006), vol. 239, No. 1, pp. 36-45 (Cited in ISR).
Pitsillides CM et al, "Selective cell targeting with light-absorbing microparticles and nanoparticles", Biophysical Journal, Elsevier, Amsterdam, NL , vol. 84, No. 6, Jun. 1, 2003 (Jun. 1, 2003), p. 4023-4032 Cited in ISR.

* cited by examiner

*Primary Examiner* — Teresa E Knight
(74) *Attorney, Agent, or Firm* — TraskBritt

(57) ABSTRACT

A method to selectively permeabilize and/or fragmentize cells. A structure comprising a material and particles able to absorb electromagnetic radiation and cells are brought at close distance from each other. Part of the particles embedded in the structure are exposed to the free surface of the structure. The structure and, in particular, the particles in the structure are irradiated with electromagnetic radiation to selectively permeabilize and/or fragmentize the cells. Furthermore, the disclosure relates to a structure for use in a photothermal process to selectively permeabilize and/or fragmentize cells.

15 Claims, 16 Drawing Sheets

Laser illumination of PLA-IOC film

Cell killing at the surface of the eye

METHOD TO SELECTIVELY PERMEABILIZE AND/OR FRAGMENTIZE CELLS

CROSS-REFERENCE TO RELATED APPLICATIONS

This application is a national phase entry under 35 U.S.C. § 371 of International Patent Application PCT/EP2022/057464, filed Mar. 22, 2022, designating the United States of America and published as International Patent Publication WO 2022/200333 A1 on Sep. 29, 2022, which claims the benefit under Article 8 of the Patent Cooperation Treaty to European Patent Application Serial No. EP21164292.1, filed Mar. 23, 2021.

TECHNICAL FIELD

The disclosure relates to a method to selectively permeabilize and/or fragmentize cells, for example, to selectively kill or ablate cells. In particular, the disclosure relates to a structure comprising particles able to absorb electromagnetic radiation and to the use of such structure in a method to selectively permeabilize and/or fragmentize cells. The structure is suitable for use in nanosurgery, for example, to kill or ablate corneal cells.

BACKGROUND

For the treatment of several diseases, like cancer, killing of cells at the surface of tissues is required. Despite major progress in cancer surgery, it remains highly challenging to remove all cancer cells from a tumor, especially when the tumor cells are intertwined with healthy tissues. It explains why adjuvant therapies, such as radiotherapy and chemotherapy are frequently preferred next to surgery.

Incomplete removal of tumors remains also a challenge in ophthalmology when dealing with aggressive cancers at the surface of the eye (conjunctiva and cornea). Especially for such type of cancers the use of adjuvant therapies is very limited. Indeed, controlling the deposition and dose of chemotherapeutics at the ocular surface is highly challenging while also in situ radiotherapy and cryotherapy show compromised outcomes.

Photodynamic therapy (PDT) and photothermal therapy (PTT) have proven to be promising approaches for cell killing. Such techniques have a high spatial precision that might even allow "single cell killing." However, a lack of control over the heat dissipation following a treatment with laser light (surface overheating) may irreversibly damage surrounding tissue.

Recently, nanoparticle sensitized laser irradiation has been explored to kill cells, for example, cancer cells. Upon laser irradiation, cells are damaged or killed through photothermal effects, such as local heating. In this approach, (free) nanoparticles are delivered to the cancer cells. As there is uncertainty about toxicological effects of nanoparticles, there might be toxicological concerns about such nanoparticle sensitized laser irradiation.

Therefore, it is of current interest to develop methods to selectively kill cells reducing or avoiding direct contact of the plasmonic nanoparticles with the cells.

BRIEF SUMMARY

Provided is a method to selectively permeabilize and/or fragmentize cells thereby avoiding the drawbacks of the prior art.

Provided is a method to selectively permeabilize and/or fragmentize cells with high spatial resolution using a structure comprising particles able to absorb electromagnetic radiation. In particular, it is an object of the disclosure to provide a method to selectively kill or ablate cells with high spatial resolution.

Further provided is a method to selectively permeabilize and/or fragmentize cells while limiting the diffusion or accumulation of the particles such as the microparticles and/or nanoparticles or material or fragments of the particles in surrounding cells or tissues.

Further provided is a method to selectively permeabilize and/or fragmentize cells not requiring direct contact between the structure and the cells, in particular, not requiring direct contact between the particles embedded in the structure and the cells. The method according to the disclosure allows selective permeabilization and/or fragmentization of cells using particles such as microparticles and/or nanoparticles, thereby reducing or avoiding uptake of the particles or material or fragments of the particles by the cells.

Further provided is a method to selectively permeabilize and/or fragmentize cells while limiting the diffusion or accumulation of the particles such as the microparticles and/or nanoparticles or material or fragments of the particles in surrounding cells or tissues.

Further provided is a method allowing fragmentization of cells, for example, to kill cells using laser pulses of low fluence.

Further provided is a method to permeabilize and/or fragmentize cells whereby the structure can simply be removed from the cells, for example, from the tissue, after irradiation (laser treatment).

Further provided is a method allowing removal of superficial tumors.

Further provided is a structure comprising particles able to absorb electromagnetic radiation for use in a method to selectively permeabilize and/or fragmentize cells, for example, to selectively kill cells, for example, corneal cells.

According to a first aspect of the disclosure, an in vitro or ex vivo method to selectively permeabilize and/or fragmentize cells is provided. The method comprises, for example, selectively killing or selective ablation of cells. The method comprises the steps of:

providing a structure comprising a material and comprising particles able to absorb electromagnetic radiation. The structure defines a volume V and a free surface S. The free surface S has a free surface area $A_S$. The particles are embedded in the material of the structure. At least a portion of the particles is partially exposed to the free surface S. Each of the particles partially exposed to the free surface S defines a particle-free surface P in the free surface S. The particle-free surface P has a particle-free surface area $A_P$. The particles are embedded in the material in such a way that the sum of the particle-free surface area $A_P$ of all particles ranges between 0.0001% and 50% of the free surface area $A_S$;

providing at least one cell, preferably a plurality of cells;

bringing the structure and the at least one cell at a distance d lower than 100 μm from each other, the distance d being the shortest distance between the at least one cell and the structure, preferably the shortest distance between the at least one cell and the free surface S of the structure;

irradiating the structure with electromagnetic radiation.

The free surface S of the structure is the total surface of the structure that is in direct contact with the environment. In case the structure is submerged in a fluid, for example, a liquid (such as a medium comprising (biological) cells) or a gas (for example, air) and the structure comprises a material that is impermeable for that fluid, the free surface S of the structure can also be defined as the total surface of the material of the structure that is or may have contact with the fluid.

The free surface S defines a free surface area $A_S$.

Preferably, the ratio of the free surface area $A_S$ of a structure to the volume of the structure, i.e., the ratio $A_S/V$, ranges between $10^{-2}$ and $10^2$ $\mu m^{-1}$, for example, between $10^{-1}$ and 50 $\mu m^{-1}$ or between 1 and 10 $\mu m^{-1}$.

The term "area" refers to the measurement of the size of a flat surface in a plane, i.e., the size of a two-dimensional object.

The term "surface area" refers to the measurement of the size of the surface of a three-dimensional shaped object.

The term "free surface area $A_S$" refers to the measurement of the size of the free surface of the structure.

The concentration of the particles able to absorb electromagnetic radiation present in the structure, according to the disclosure, ranges preferably between 0.001 vol % and 20 vol % (volume particles/volume structure). More preferably, the concentration of particles able to absorb electromagnetic radiation present in the structure, according to the disclosure, ranges between 0.01 vol % and 10 vol % or between 0.01 vol % and 5 vol % and is, for example, 0.05 vol %, 0.1 vol %, 0.2 vol %, 0.5 vol %, 1 vol %, 2 vol % or 5 vol %.

As mentioned above, a portion of the particles present in the structure is partially exposed to the free surface S of the structure. Such particles are thus partially embedded in the material and partially exposed to the free surface S of the structure. It is clear that a structure, according to the disclosure, may comprise in addition to the particles partially exposed to the free surface S, particles that are fully embedded by the material of the structure.

Each of the particles partially exposed to the free surface S has a free surface that is part of the free surface S. The free surface S that is occupied by such particle partially exposed to the free surface S is referred to as the particle-free surface P. The particle-free surface P has a particle-free surface area $A_p$.

The term "particle-free surface area $A_p$" refers to the measurement of the size of the particle-free surface P.

The particles that are partially exposed to the free surface S of the structure may either protrude or not protrude from the material. Particles that are protruding, protrude from the outer surface defined by the material.

A structure according to the disclosure may comprise a combination of particles partially exposed to the free surface S of the structure that are protruding from the outer surface defined by the material and particles partially exposed to the free surface S of the structure that are not protruding from the outer surface defined by the material.

Particles that are protruding, extend, for example, to a height of 50 $\mu m$, for example, a height of 0.5 $\mu m$ to 10 $\mu m$, measured perpendicular to the surface of the material.

Preferably, the particles are embedded in the structure, more particularly in the material of the structure in such a way that the sum of the particle-free surface area $A_p$ of all particles ranges between 0.0001% and 50% of the free surface area $A_S$ as indicated below:

$$0.0001 < \frac{\sum_i (A_p)_i}{A_S} \cdot 100 < 50$$

with i ranging from 1 to n (n being the number of particles partially exposed to the free surface S).

In preferred embodiments, the particles are embedded in the structure, in such a way that the sum of the particle-free surface area $A_p$ of all particles ranges between 1% and 25% of the free surface area $A_S$, between 5% and 25% of the free surface area $A_S$, between 15% and 25% of the free surface area $A_S$. The sum of the particle-free surface area $A_p$ of all particles is, for example, 20% of the free surface area $A_S$.

Upon irradiation of the structure with electromagnetic radiation, the particles present in the structure, in particular, the particles that are partially exposed to the free surface S of the structure, cause a photothermal effect. This photothermal effect causes, in particular, a local and temporary heating of the material close to an irradiated particle and induces the formation of vapor bubbles, for example, vapor microbubbles or vapor nanobubbles. Such vapor bubbles may cause permeabilization or fragmentation of a cell that is at short distance.

In embodiments of the disclosure, the method allows increasing the permeability of cells by bringing the cells and the structure in contact with each other or at a short distance from each other and by irradiating the structure, in particular, by irradiating the particles present in the structure that are partially exposed to the free surface S with electromagnetic radiation. The method allows increasing the permeability of cells without requiring direct contact between the particles and the cells.

In other embodiments of the disclosure, the method allows fragmentization of cells by bringing the cells and the structure in contact with each other or at short distance from each other and by irradiating the structure, in particular, by irradiating the particles present in the structure that are partially exposed to the free surface S with electromagnetic radiation. The method allows fragmentization of cells without requiring direct contact between the particles and the cells. The method allows killing or ablation of cells by bringing the cells and the structure in contact with each other or at short distance from each other and by irradiating the structure, in particular, the particles that are partially exposed to the free surface S with electromagnetic radiation. In particular, the method allows killing or ablation of cells without requiring direct contact between the particles and the cells.

In further embodiments of the disclosure, the method allows increasing the permeability of particular cells while fragmentizing other cells by bringing the cells and the structure in contact with each other or at short distance from each other and by irradiating the structure, in particular, by irradiating the particles present in the structure that are partially exposed to the free surface S with electromagnetic radiation. In particular, the method allows increasing the permeability of particular cells while fragmentizing other cells without requiring direct contact between the particles and the cells.

Bringing a cell and the structure in contact with each other means that there is direct contact between the cell and the structure. In such case, the cell contacts the free surface S of the structure. A cell can be in direct contact with the material of the structure and/or in direct contact with one or more particles partially exposed to the free surface S of the structure.

Bringing a cell and the structure at short distance from each other means that the shortest distance d between a cell and the structure, in particular, the shortest distance between a cell and the free surface S of the structure, is 100 $\mu m$ or less than 100 $\mu m$. The shortest distance d between a cell and the structure is, for example, 50 µm, 20 µm, 10 µm, 5 µm, 3 µm, 2 µm, 1 µm, 0.5 µm or 0.1 µm. Preferably, the shortest distance d between a cell and a particle partially exposed to the free surface S of the structure is 100 µm or less than 100 µm. The closest distance between a cell and a particle partially exposed to the free surface S of the structure is, for example, 50 µm, 20 µm, 10 µm, 5 µm, 3 µm, 2 µm, 1 µm, 0.5 µm or 0.1 µm.

The at least one cell comprises, for example, a suspension of cells or a tissue of cells. Examples of tissues comprise ocular tissues or skin tissues. Particular examples comprise tumor margins.

To allow spatially selective permeabilization and/or fragmentation at single cell resolution, the density of the particles at least partially exposed to the free surface S should be chosen so that each cell is sufficiently close to a particle at least partially exposed to the free surface S.

The density of cells brought at a distance d equal to or lower than 100 µm is, for example, ranging between 1 cells/mm$^2$ and $10^5$ cells/mm$^2$, for example, ranging between 10 cells/mm$^2$ and $10^4$ cells/mm$^2$, between $10^2$ cells/mm$^2$ and $10^4$ cells/mm$^2$ or between $10^3$ cells/mm$^2$ and $3.10^3$ cells/mm$^2$.

The density of the particles being partially exposed to the free surface S of the structure ranges preferably between 1 particle/100 µm$^2$ and 10 particles/100 µm$^2$, for example, between 1 particle/µm$^2$ and 5 particles/100 µm$^2$, for example, 2 particles/µm$^2$, 3 particles/100 µm$^2$ or 4 particles/100 µm$^2$.

The particles that are embedded in a structure according to the disclosure, may comprise any particle able to absorb electromagnetic radiation and adapted to generate a photothermal effect upon irradiation with electromagnetic radiation.

The term "particle" as used herein refers to a particle or a group, agglomerate, or cluster of two or more particles having dimensions (more particularly, the largest dimensions of the particles) of about 1 nm to about 40000 nm (40 µm), for example, from 1 nm to 10000 nm (10 µm), from 10 nm to 2000 nm (2 µm), from 50 nm to 1000 nm (1 µm) or from 100 nm to 500 nm, for example, 200 nm.

The dimensions are preferably measured by measuring the largest dimensions of the particles. The largest dimension of a particle corresponds with the largest distance between two points of that particle. The largest dimension of a particle refers, for example, to the width (largest width), height (largest height) or diameter (largest diameter) of that particle.

An alternative way to specify the size of the particles is by the equivalent spherical diameter (also referred to as the equivalent volume diameter). The equivalent spherical diameter (or ESD) of an irregularly shaped object is the diameter of a sphere of equivalent volume. In embodiments, the particles may have an equivalent spherical diameter of about 1 nm to about 40000 nm (40 µm). In embodiments, the particles may have an equivalent spherical diameter of about 1 nm to about 10000 nm (10 µm). For instance, the particles may have an equivalent spherical diameter of about 10 nm to 200 nm (2 µm), from 50 nm to 1000 nm (1 µm), or from 100 nm to 500 nm, for example, 200 nm.

The dimensions of a particle (for example, width, height or diameter of a particle), in particular, the largest dimensions of a particle (for example, the largest width, height or diameter of a particle) or the equivalent spherical diameter can be determined using Transmission Electron Microscopy (TEM), Scanning Electron Microscopy (SEM) or atomic force microscopy (AFM).

For the purpose of this disclosure, the terms "group of particles," "agglomerate of particles," and "cluster of particles" are interchangeably used.

A cluster of particles comprises at least two individual particles, preferably between 10 and 1000 individual particles, for example, between 100 and 1000 individual particles. An individual particle of a cluster is preferably contacting at least one individual particle of a cluster or is positioned at a distance of a few micrometers of another individual particle of that cluster.

In case the particles comprise clusters, the individual particles of a cluster have preferably dimensions (more particularly, the largest dimensions of the individual particles) of about 1 nm to about 200 nm, for example, from 50 nm to 100 nm.

A cluster has preferably dimensions (more particularly, the largest dimensions of the cluster) of about 1000 nm to about 40000 nm (10 µm), for example, from 10 nm to 2000 nm, from 50 nm to 1000 nm or from 100 nm to 500 nm, for example, 200 nm.

The term "microparticle" as used herein refers to a particle or a group, agglomerate, or cluster of two or more particles having dimensions (more particularly, the largest dimensions of the particles) of more than 1000 nm (>1 µm) and at most 10000 nm (≤10 µm). In case a microparticle comprises a cluster, the individual particles of such cluster have preferably dimensions (more particularly, the largest dimensions of the individual particles) of about 1 nm to about 200 nm, for example, from 50 nm to 100 nm.

The term "nanoparticle" refers to a particle or a group, agglomerate, or cluster of two or more particles having dimensions (largest dimensions of the particles) of at least 1 nm (≥1 nm) and at most 1000 nm (≤1 µm). In case a microparticle comprises a cluster, the individual particles of such cluster have preferably dimensions (more particularly, the largest dimensions of the individual particles) of about 1 nm to about 200 nm, for example, from 50 nm to 100 nm.

Particles having dimensions (largest dimensions of the particles) ranging between 100 nm and 1000 nm might also be referred to as "submicronic particles."

The particles may have any shape. They may, for example, be spherical, elliptical, rod-like shaped, pyramidal, branched, or may have an irregular shape.

The particles may be solid particles, may have a shell structure or a core-shell structure comprising one or more materials.

Preferred particles comprise metal particles, metal oxide particles, carbon or carbon-based particles, particles comprising one or more light absorbing compounds or particles loaded or functionalized with one or more light absorbing compounds.

Examples of metal particles comprise gold particles, silver particles, platinum particles, palladium particles, copper particles and alloys thereof. Preferred metal particles comprise gold particles, silver particles and alloys thereof.

Examples of metal oxide particles comprise iron oxide, titanium oxide, zirconium oxide, cerium oxide, zinc oxide and magnesium oxide.

Examples of carbon or carbon-based particles comprise graphene quantum dots, (reduced) graphene oxide and carbon nanotubes.

Examples of particles comprising one or more light absorbing compounds or particles loaded or functionalized with one or more light absorbing compounds comprise particles comprising, loaded or functionalized with synthetic organic or inorganic absorbers as well as particles comprising, loaded or functionalized with naturally occurring absorbers or derivatives thereof. Particular examples comprise liposomes, solid lipid nanoparticles, polymer-based particles comprising loaded or functionalized with light absorbing dye molecules such as indocyanine green, inorganic quantum dots (having low fluorescence quantum yield), naturally occurring light absorbers like pigments (such as melanin, rhodopsin, photopsins or iodopsin) and synthetic analogs like polydopamine, or photosensitizers used in photodynamic therapy.

In embodiments of the method or products according to the disclosure, the particles may be biodegradable. In embodiments, the particles may be biocompatible. In embodiments, the particles may be biodegradable and biocompatible. In embodiments, the particles may comprise or consist of clinically approved components. Advantageously, the particles are biodegradable, biocompatible and comprise or consist of clinically approved components.

A structure according to the disclosure may comprise one type of particles or a combination of different particles, for example, particles having a different size, a different composition and/or a different shape.

The material of the structure into which the particles able to absorb electromagnetic radiation are embedded comprises, for example, an inorganic material or an inorganic-based material, for example, silica or a silica-based material or a ceramic or ceramic-based material, an organic material or organic-based material, such as a carbon or carbon-based material or a polymer or polymer-based material. The material of the structure may also comprise a composite material comprising at least one of the above-mentioned materials, for example, a composite material comprising an organic and an inorganic material.

Preferred materials of the structure comprise or are based on polystyrene, polycaprolacton, ethylcellulose, cellulose acetophthalate, polylactic acid, polylactic-co-glycolic acid, cellulose, polyvinyl alcohol, polyethylene glycol, gelatin, collagen, silk, alginate, hyaluronic acid, dextran, starch, polycarbonate or polyacrylate. In other embodiments, the material of the structure comprises a gel or a hydrogel. A gel comprises a nonfluid polymer that is expanded throughout its whole volume by a fluid. A hydrogel is a gel in which the swelling agent is water. In particular, a hydrogel is a three-dimensional network of (hydrophilic) polymer that can swell in water and that can hold a large amount of water while maintaining its structure due to chemical or physical cross-linking of individual polymer chains. Hydrogels may comprise homopolymers, copolymers, semi-interpenetrating networks and interpenetrating networks.

In preferred embodiments, the structure comprises a surface modified material, for example, a surface modified polymer material. The surface modification comprises, for example, the application of a coating, for example, a protein coating, a coating comprising antibodies, a coating comprising lipids, a polymer coating, or combinations thereof.

The material is preferably transparent for visible light. Preferably, the material has a transmittance for visible light having a wavelength ranging between 450 and 650 nm of at least 50% or a transmittance for visible light having a wavelength ranging between 450 and 650 nm of at least 60%.

Preferably, the structure comprising the material and the particles has a transmittance for visible light having a wavelength ranging between 450 and 650 nm of at least 25%, a transmittance for visible light having a wavelength ranging between 450 and 650 nm of at least 35% or a transmittance for visible light having a wavelength ranging between 450 nm and 650 nm of at least 50%.

The structure comprising the material and the particles embedded in the material may comprise a continuous or discontinuous structure.

The structure may be rigid or flexible. A flexible structure can be preferred as such structure can be adapted to conform the surface of the tissue to be treated.

The structure may be flat or planar or the structure may be non-flat, for example, curved.

The structure can have a flat or non-flat outer surface.

The structure may comprise a porous or non-porous structure.

For some applications, porous structures are preferred as they have the advantage to have a high free surface area $A_s$ and thus have a large surface area available to be exposed to cells that are introduced on or near the structure according to the method of the disclosure. Preferably, such porous structure has a pore size that allows partial or complete penetration of the cells introduced on or near the structure into the pores. Preferably, the porous structure has a pore size that does not restrict access of molecules present in the cell medium to the cells.

The porosity of a structure is defined as the ratio of the volume of the pores or voids of a structure over the total volume occupied by that structure, i.e., the sum of the volume V of the structure (the volume of the material and the particles embedded in the material) and the volume of the pores or voids of that structure. The porosity may range between 0% and 100%. In case the structure comprises a porous structure the porosity of the structure is preferably at least 50%, at least 60% at least 80%, at least 90%, at least 95% or at least 99%.

A first group of structures according to the disclosure comprises films or foils comprising particles able to absorb electromagnetic radiation embedded in the films or foils. Such films or foils are, for example, non-porous. Examples comprise polymer films or polymer foils comprising particles able to absorb electromagnetic radiation embedded in the polymer film or polymer foil. For the purpose of this disclosure, the terms "film" and "foil" are used interchangeably.

Preferred examples of films comprise polymer films comprising or based on polystyrene, polycaprolacton, ethylcellulose, cellulose acetophthalate, polylactic, polylactic-co-glycolic acid, cellulose, polyvinylalcohol, polyethylene glycol, gelatin, collagen, silk, alginate, hyaluronic acid, dextran, starch, polycarbonate or polyacrylate having iron oxide particles and/or carbon particles embedded in the polymer films. The polymer films have, for example, a thickness ranging between 0.1 µm and 100 µm, for example, between 0.1 µm and 10 µm.

Preferably, such film defines a first surface S1 and a second surface S2, opposite to the first surface S1. The first surface S1 defines a first free surface area $A_{S1}$ and the second surface S2 defines a second free surface area $A_{S2}$. The first surface is, for example, the top surface (defining a top free surface area) while the second surface is the bottom surface (defining a bottom free surface area). Alternatively, the first surface is the bottom surface (defining a bottom free surface area) while the second surface is the top surface (defining a top free surface area).

When irradiated, the radiation impinges, for example, on the first surface S1 or on the second surface S2.

Preferably, the first free surface area $A_{S1}$ and the second free surface area $A_{S2}$ have the same or substantially the same size.

The structures of the first group have, for example, a thickness t, a length l and a width w. The thickness ranges preferably between 0.1 µm and 10 µm, for example, between 0.1 µm and 10 µm. The volume V of the structure corresponds with t·l·w or with t·$A_{S1}$. As the length l and the width w of the structures of the first group are typically substantially larger than the thickness to of the structure, the free surface area $A_S$ of the structure can be estimated as $A_{S1}+A_{S2}$. The free surface that is irradiated usually corresponds with one of the surfaces of the structure (for example, the first surface S1 or the second surface S2) and can be estimated as being AS1. Consequently, the ratio of the free surface area of the structure over the volume of the structure, i.e., S/V, corresponds with 1/t.

Preferably, at least one of the first surface S1 or the second surface S2 comprises particles at least partially exposed the free surface S of the structure. Each of the particles partially exposed to the first surface S1 or to the second surface S2 defines a particle-free surface P in the first surface S1 or in the second surface S2. The particle-free surface P has a particle-free surface area $A_P$. The particles are embedded in the material in such a way that the sum of the particle-free surface area $A_P$ of all particles partially exposed to the first surface S1 or partially exposed to the second surface S2 ranges between 0.0001% and 50% of the sum of the free surface area $A_{S1}$ and the free surface area $A_{S2}$. More preferably, the particles are embedded in the material in such a way that the sum of the particle-free surface area $A_P$ of all particles partially exposed to the first surface S1 or partially exposed to the second surface S2 ranges between 5% and 25% of the sum of the free surface area $A_{S1}$ and the free surface area $A_{S2}$ or between 15% and 25% of the sum of the free surface area $A_{S1}$ and the free surface area $A_{S2}$.

In particular embodiments, one of the first surface S1 or the second surface S2 comprises particles at least partially exposed to the free surface S of the structure. Each of the particles partially exposed to the first surface S1 defines a particle-free surface P in the first surface S1. The particle-free surface P has a particle-free surface area $A_P$. The particles are embedded in the material in such a way that the sum of the particle-free surface area $A_P$ of all particles partially exposed to the first surface S1 ranges between 0.0001% and 50% of the free surface area $A_{S1}$.

In preferred embodiments, the particles are embedded in the material in such a way that the sum of the particle-free surface area $A_P$ of all particles partially exposed to the first surface S1 ranges between 5% and 25% of the free surface area $A_{S1}$ or between 15% and 25% of the free surface area $A_{S1}$.

A second group of structures according to the disclosure comprises hydrogels comprising particles able to absorb electromagnetic radiation embedded in the hydrogels.

Preferred hydrogels comprise homopolymers, copolymers, semi-interpenetrating networks and interpenetrating networks. Examples of polymers comprise poly(2-hydroxyethyl methacrylate) (PHEMA), 2-hydroxyethyl methacrylate ((HEMA), polyethylene glycol (PEG), polyethylene glycol methacrylate (PEG-MA), methacrylic acid (MAA); carboxymethyl cellulose (CMC); polyvinylpyrrolidone (PVP), acrylamide/acrylic acid copolymer poly(N-isopropyl acrylamide) (PNIPAM), chitosan, acrylate-modified PEG, acrylate-modified hyaluronic acid, heparin and amine end-functionalized 4-arm star-PEG. Examples of cross-linkers comprise polyethylene glycol dimethacrylate, triethylene glycol dimethacrylate (TEGDMA), tetra(ethylene glycol) dimethacrylate and N,N'-methylene bisacrylamide.

The particles comprise, for example, iron oxide particles and/or carbon particles.

A third group of structures according to the disclosure comprises porous structures comprising a material and particles able to absorb electromagnetic radiation embedded in the material. Examples comprise porous polymer structures with the particles embedded in the porous polymer structure. Examples of porous structures comprise structures comprising fibers (for example, polymer fibers), structures comprising particulates (for example, polymer particulates), structures comprising a combination of fibers and particulates (for example, a combination of polymer fibers and/or polymer particulates) and structures comprising foam (for example, polymer foam). The fibers and/or particulates can be interconnected or not. The particulates such as, for example, the polymer particulates, may comprise spherical particulates as well as irregular-shaped particulates. The particles embedded in the porous structure comprise, for example, iron oxide particles and/or carbon particles.

A first example of a structure of the third group is a structure comprising (polymer) fibers. The (polymer) fibers have, for example, a fiber diameter ranging between 0.1 µm and 10 µm, for example, a diameter of 0.5 µm or 1 µm. The (polymer) fibers can be interconnected or not. The (polymer) fibers can be obtained by any technique known in the art. A preferred technique to manufacture the (polymer) fibers is electrospinning. Alternative techniques comprise wet spinning, melt spinning, extrusion spinning, dry spray wet spinning, emulsion spinning and suspension spinning. Preferred examples of polymer comprise polystyrene fibers, polycaprolacton fibers, ethylcellulose fibers, cellulose acetophthalate fibers, polylactic acid fibers and polylactic-co-glycolic acid-based fibers. The (polymer) fibers can be surface modified.

As the (polymer) fibers can be considered as long cylinders with a diameter corresponding to the fiber diameter $d_{fiber}$ and a length corresponding to the length of the fiber $L_{fiber}$, the volume of the fiber $V_{fiber}$ corresponds with $$\pi \left(\frac{d_{fiber}}{2}\right)^2 L_{fiber}$$

and the free surface area of the fiber $S_{fiber}$ corresponds with $\pi d_{fiber} L_{fiber}$. Consequently, the ratio of the free are surface $S_{fiber}$ to the volume $V_{fiber}$ corresponds with $4/d_{fiber}$.

A second example of a structure of the third group is a structure comprising polymer particulates such as, for example, polymer (micro)spheres. The particulates have, for example, a particulate diameter ranging between 0.1 µm and 10 µm, for example, a diameter of 0.5 µm or 1 µm. The polymer particulates can be interconnected or not. The (polymer) particulates can be obtained by any technique known in the art. Preferred examples of particulates comprise polystyrene, polycaprolacton, ethylcellulose, cellulose acetophthalate, polylactic acid, polylactic-co-glycolic acid-based fibers. The polymer particulates can be surface modified.

In case the particulates are microspheres with a diameter $d_{ms}$, the volume of the microspheres $V_{ms}$ corresponds to $$\frac{4}{3}\pi \left(\frac{d_{ms}}{2}\right)^3$$

and the free surface area of the microspheres $S_{ms}$ corresponds to $$4\pi\left(\frac{d_{ms}}{2}\right)^2.$$

Consequently, the ratio of the free surface area $S_{ms}$ over the volume of the microspheres $V_{ms}$ is $6/d_{ms}$.

As mentioned above, the method according to the disclosure comprises the step of bringing the structure and the at least one cell at a distance d lower than 100 μm from each other.

The at least one cell comprises, for example, a plurality of cells, for example, a suspension comprising cells or a tissue of cells.

The structure and the at least one cell can be brought at a distance d from each other by bringing the at least one cell on or close to the structure or by bringing the structure close to the at least one cell.

The cells are, for example, introduced on or near the structure by applying a suspension comprising cells on or near the structure, in particular, on or near the free surface S of the structure. The cells can either be introduced continuously on or near the structure or discontinuously on or near the structure.

The concentration of the cells in the suspension ranges preferably between 1 and $10^6$ cells per mL, for example, between $10^3$ and $10^5$ cells per mL.

In preferred methods the suspension, i.e., the cells of the suspension, are cultured on or near the structure during a certain time period.

In alternative methods the cells are treated by activation of the structure with electromagnetic irradiation immediately or shortly after their introduction on or near the structure.

In embodiments of the disclosure, after introducing the at least one cell on or near the structure, the at least one cell may be incubated before (i.e., prior to) the irradiation step, for example, during one or more minutes or during one or more hours.

Alternatively, the structure can be brought close to the at least one cell, for example, by applying the structure on a tissue comprising cells or at short distance from a tissue comprising cells, the free surface S of the structure is thereby in contact with the cells or at a distance d from the cells.

The structure and, in particular, the particles partially exposed to the free surface S of the structure is/are preferably irradiated with electromagnetic radiation, for example, with a pulsed radiation source, although irradiation by a continuous wave radiation source can also be considered.

The terms "radiation" and "electromagnetic radiation" may be used interchangeably herein.

The wavelength of the radiation source may range from the ultraviolet region to the infrared region. In preferred methods, the wavelength range of the radiation used is in the visible to the infrared region, including the near infrared region.

The electromagnetic radiation may be generated by a laser, such as a pulsed laser. Laser irradiation, such as irradiation by pulsed lasers, e.g., pico-, femto- and/or nanosecond pulsed lasers, can be combined with a structure in accordance with embodiments of the disclosure to efficiently permeabilize a cell's barrier, e.g., by laser-induced vapor nanobubble generation. While laser irradiation may be advantageous, irradiation by another (intense) light source is not necessarily excluded to achieve the same or similar effects.

The wavelength of the radiation source may range from the ultraviolet region to the infrared region. In preferred methods, the wavelength range of the radiation used is in the visible to the near infrared region.

When a pulsed radiation source is used, the pulses preferably have a duration in the range of 1 fs and 1 ms, for example, in the range of 1 fs and 100 μs, in the range of 10 fs and 10 μs, in the range of 100 fs and 1 μs or in the range of 1 ps and 100 ns.

The laser pulses may consist of 1 to 1000 laser pulses, such as 1 to 500 laser pulses, 1 to 100 laser pulses, 1 to 20 laser pulses, or 1 to 10 laser pulses (per cell or per cell sample). The number of laser pulses may be, for example, dependent upon the photoresponsive organic particle and the type of cells.

The fluence (electromagnetic energy delivered per unit area) per pulse of the radiation source ranges preferably between 0.0001 J/cm² and 1000 J/cm², for example, between 0.001 J/cm² and 100 J/cm², between 0.01 J/cm² and 10 J/cm², between 0.1 J/cm² and 10 J/cm², for example, 0.1 J/cm², 1 J/cm² or 5 J/cm².

An advantage of the method according to the disclosure is that fragmentation or release of the particles embedded in the structure is reduced or avoided. ICP-MS analysis demonstrated that no detectable amounts of the material of the particles are released.

Another advantage of the method according to the disclosure is the spatial resolution of the method allowing permeabilization and/or fragmentization of a single cell.

A further advantage of the method according to the disclosure is that direct contact between the structure and the cells, in particular, between the particles and the cells is not required to permeabilize and/or fragmentize cells thereby reducing or avoiding uptake of the particles or fragments of the particles by the cells.

Still a further advantage of the method according to the disclosure is the ease of fabrication of the structure.

The methods as taught herein may as well be useful to selectively permeabilize and/or fragmentize a cell or cells of a human or animal body.

According to a second aspect of the disclosure, a structure as described above for use in a photothermal process to selectively permeabilize and/or fragmentize cells in contact or close to the structure is provided. The structure comprises a material and comprises particles able to absorb electromagnetic radiation. The structure defines a volume V and a free surface S. The free surface S has a fee surface area $A_S$. The particles are embedded in the material. At least a portion of the particles is partially exposed to the free surface S. Each of the particles partially exposed to the free surface S defines a particle-free surface P in the free surface S. The particle-free surface P has a particle-free surface area $A_P$. The particles are embedded in the material in such a way that the sum of the particle-free surface area $A_P$ of all particles ranges between 0.0001% and 50% of the free surface area $A_S$.

The photothermal process comprises the steps of:
  bringing the structure and the at least one cell at a distance
    d lower than 100 μm from each other, the distance d
    being the shortest distance between the at least one cell
    and the structure, in particular, the shortest distance
    between the at least one cell and the free area surface
    S of the structure;
  irradiating the structure with electromagnetic radiation to
    selectively permeabilize and/or fragmentize the at least
    one cell.

The structure according to the disclosure is, in particular, suitable for use in a photothermal process in a method of therapy in a subject to selectively permeabilize and/or fragmentize cells of the subject, the method comprising:

bringing the structure at a distance d lower than 100 µm from at least one cell of the subject, the distance d being the shortest distance between the at least one cell of the subject and the structure, in particular, the shortest distance between the at least one cell and the free area surface S of the structure;

irradiating the structure with electromagnetic radiation to selectively permeabilize and/or fragmentize the at least one cell.

The at least one cell comprises preferably a suspension of cells or a tissue of cells. Examples of tissues comprise ocular tissues or skin tissues. Particular examples comprise tumor margins.

The method of treatment comprises, for example, nanosurgery. A particular treatment comprises the killing or ablation of corneal cells.

The structure and process as taught herein allow treatment, such as laser-assisted treatment, of a disease or condition in a subject.

The terms "subject," "individual" or "patient" may be used interchangeably herein, and typically and preferably denote humans, but may also encompass reference to non-human animals, preferably warm-blooded animals, even more preferably mammals.

Any of the above-described structures can be considered for use in a photothermal process in a method of therapy in a subject to selectively permeabilize and/or fragmentize cells of the subject.

The electromagnetic radiation can be generated by any source described above. Preferably, the electromagnetic radiation comprises pulsed radiation generated by a laser.

In preferred methods, a structure, according to the disclosure, is brought at close distance from cells, for example, from a tissue of cells, before being irradiated. Such method is referred to as "structure on top of cells." In such method, the structure can easily be removed after irradiation.

In particularly preferred methods, a film, for example, a polymer film comprising particles able to absorb electromagnetic radiation, is brought at close distance from cells, for example, from a tissue of cells, before being irradiated ("film on top of cells").

In alternative methods, cells are applied on the structure, for example, grown on a structure before being irradiated. Such method is referred to as "cells on top of structure."

In particularly preferred methods, a film, cells are applied on a film, for example, on a polymer film comprising particles able to absorb electromagnetic radiation before being irradiated ("cells on top of film"). Cells are, for example, grown on a film, for example, on a polymer film comprising particles able to absorb electromagnetic radiation.

BRIEF DESCRIPTION OF THE DRAWINGS

The disclosure will be discussed in more detail below, with reference to the attached drawings, in which.

DETAILED DESCRIPTION

Figure 1A:
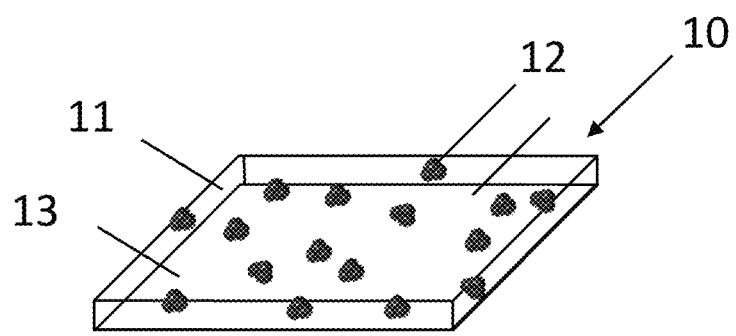
FIG. 1A shows a schematic illustration of a structure to selectively permeabilize and/or fragmentize cells according to the disclosure.

The disclosure will be described with respect to particular embodiments and with reference to certain drawings, but the disclosure is not limited thereto but only by the claims. The drawings are only schematic and are non-limiting. The size of some of the elements in the drawing may be exaggerated and not drawn on scale for illustrative purposes. The dimensions and the relative dimensions do not correspond to actual reductions to practice of the disclosure.

When referring to the endpoints of a range, the endpoints values of the range are included.

When describing the disclosure, the terms used are construed in accordance with the following definitions, unless indicated otherwise.

The terms "first," "second," and the like, used in the description as well as in the claims, are used to distinguish between similar elements and not necessarily describe a sequence, either temporally, spatially, in ranking or in any other manner. It is to be understood that the terms so used are interchangeable under appropriate circumstances and that the embodiments of the disclosure described herein are capable of operation in other sequences than described or illustrated herein.

The term "and/or" when listing two or more items, means that any one of the listed items can by employed by itself or that any combination of two or more of the listed items can be employed.

The term "area" refers to the measurement of the size of a flat surface in a plane, i.e., the size of a two-dimensional object.

The term "surface area" refers to the measurement of the size of the surface of a three-dimensional shaped object.

The term "cell" refers to all types of biological cells, including eukaryotic cells an prokaryotic cells. The cell may refer to a human cell, an animal cell and a plant cell.

The term "fragmentize" refers to any way to break, cut or otherwise separate something into fragments. Fragmentize cells refers to any way to break, cut or otherwise separate cells into fragments and includes killing of cells and ablation of cells.

The terms "increase the permeability of," "permeabilize," "permeabilizing" and "permeabilization" refer to any way to alter the permeability of a cell, in particular, the permeability of a membrane or barrier of a cell, for example, the plasma membrane of a cell, at least partially or locally. After permeabilization, the membrane or barrier, for example, the plasma membrane of a cell is altered in such a way that it is more permeable for one or more types of compounds as, for example, molecules, macromolecules, particles or nanoparticles.

The terms "perforate," "perforating" or "perforation" refer to any way to provide a membrane or barrier, for example, the plasma membrane of a cell, with one or more openings, holes or pores. By perforating a membrane or barrier, for example, the plasma membrane of a cell, openings are created into the membrane or barrier, for example, the plasma membrane of a cell, allowing the transport of compounds, such as molecules, macromolecules, particles or nanoparticles across the membrane or barrier, for example, across the plasma membrane of a cell.

For the purpose of this disclosure, the terms "increase the permeability of," "permeabilize," "permeabilizing" and "permeabilization" and the terms "perforate," "perforating" and "perforation" are interchangeably used. Similarly, the terms "opening," "hole" and "pore" may be used interchangeably.

The term "generation of a vapor bubble" includes expansion of the vapor bubble, collapse of the vapor bubble or a combination of expansion and collapse of the vapor bubble and secondary effects that can be the result of the bubble expansion and collapse, such as pressure waves and flow of the surrounding medium.

The term "vapor bubble" or "bubble" refers to vapor nanobubbles and vapor microbubbles. Preferably, the term "vapor bubble" or "bubble" refers to vapor bubbles having a diameter in the range of 10 nm to 100 µm. Vapor bubbles comprise water vapor bubbles, although embodiments are not limited thereto.

EXPERIMENTAL RESULTS

Example 1

An embodiment of a structure 10, according to the disclosure, comprising a film comprising polymer material 11 and particles 12 able to absorb electromagnetic radiation is shown in FIG. 1A. A portion of the particles is partially exposed to one surface, for example, the top surface 13 of the structure. The particles are embedded in such a way that the sum of the particle-free surface area $A_P$ of all particles ranges between 0.0001% and 50% of the free surface area $A_S$, more preferably between 5% and 25% of the free surface area As or between 15% and 25% of the free surface area $A_S$. More particularly, the particles are embedded in such a way that the sum of the particle-free surface area $A_P$ of all particles ranges between 0.0001% and 50% of the top free surface area $A_{S1}$, more preferably between 5% and 25% of the free surface area As1 or between 15% and 25% of the free surface area $A_{S1}$.

Figure 1B:
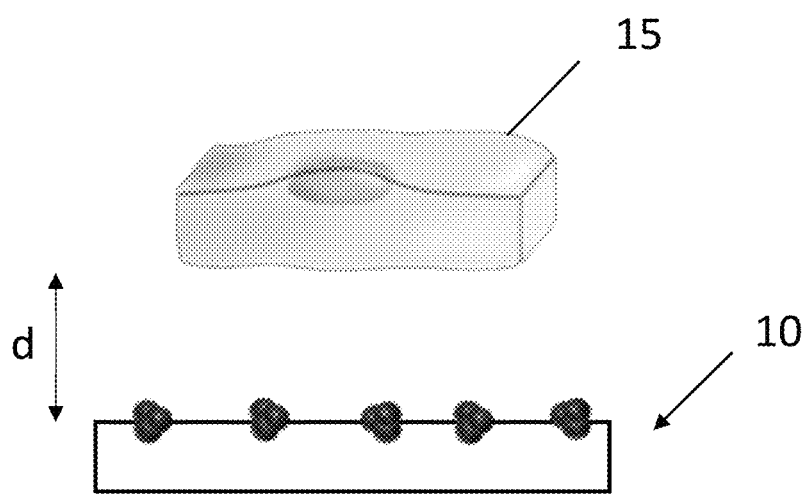
FIG. 1B shows the cross-section of the structure shown in FIG. 1A with a cell positioned at a distance d from the structure.

FIG. 1B shows the structure of FIG. 1A with a cell 15 or a plurality of cells 15 at short distance d from the structure 10.

The below described examples comprise polylactic acid (PLA) as material of the structure and comprise iron oxide particles as particles able to absorb electromagnetic radiation.

Figure 2:
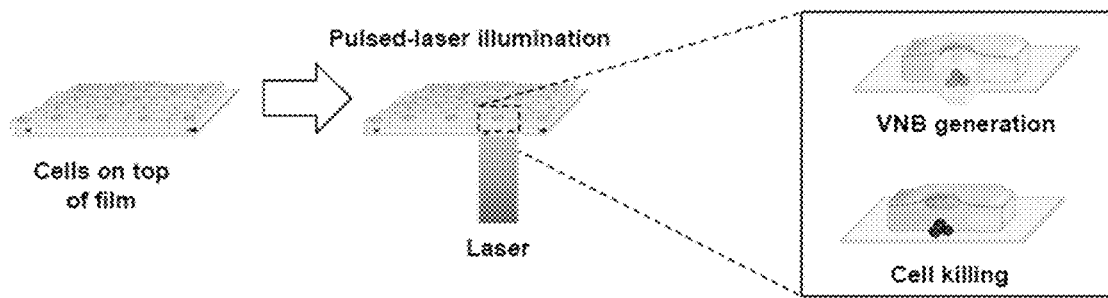
FIGS. 2 and 3 schematically illustrate the method to selectively permeabilize and/or fragmentize cells according to the disclosure, whereby cells are grown on a film ("cells on top of film") as shown in FIG. 2 and a film is applied on a cell layer ("film on top of cells") as shown in FIG. 3.
Figure 3:
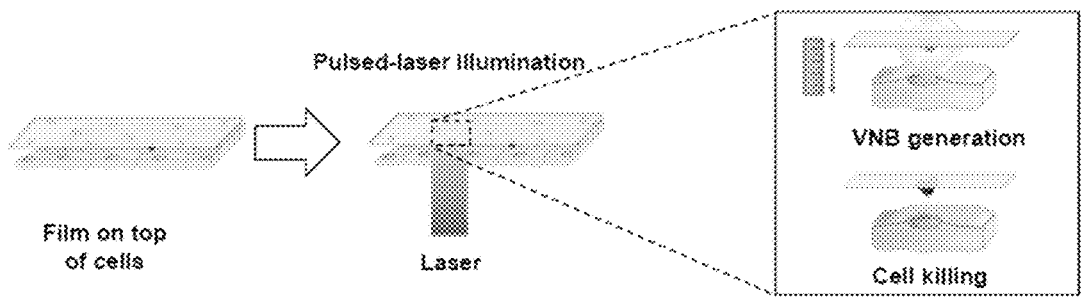

It is clear that other materials and other particles can be considered as well. To evaluate whether vapor bubbles generated at the surface of such structure can permeabilize and/or fragmentize cells in contact or at short distance d from a cell or from a plurality of cells (FIG. 1B), two types of experiments were performed:

cells were grown on top of the structure and the structure (more particularly, the particles in the structure) are irradiated with (pulsed) electromagnetic radiation ("cells on top of the structure") (FIG. 2);

a structure was applied on a cell layer and the structure (more particularly, the particles in the structure) is radiated with (pulsed) electromagnetic radiation ("structure on top of the cells") (FIG. 3).

Figure 4:
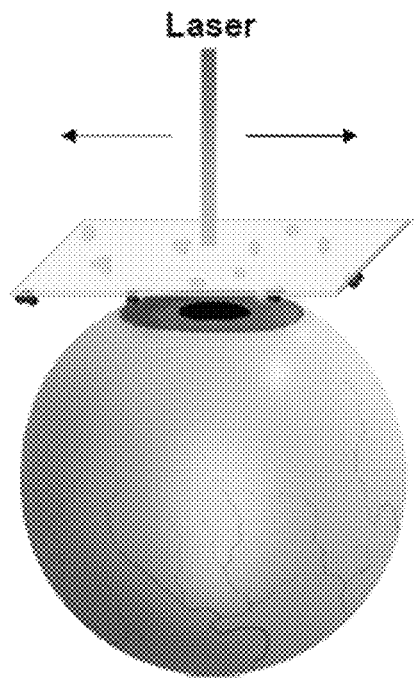
FIG. 4 illustrates a method whereby a structure comprising particles is applied on the cornea of a bovine eye before being irradiated with a pulsed laser.
Figure 4:
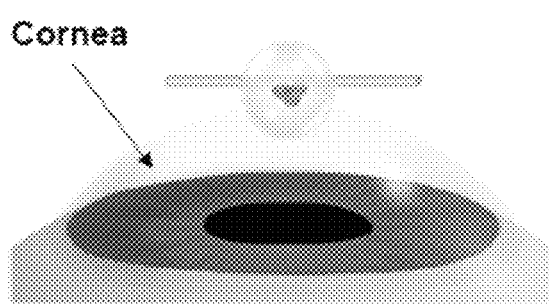

Furthermore, a structure comprising particles was applied on the cornea of a bovine eye and irradiated with a pulsed laser (FIG. 4).

1. Materials and Methods

1.1 Materials

Iron oxide ($Fe_3O_4$) nanoparticles (IONPs) with a size of 50-100 nm, polylactic acid (PLA) with a molecular weight (Mw) of 80 kDa, FITC-dextrans of 500 kDa and chloroform were all purchased from Sigma-Aldrich (Belgium). Calcein AM and propidium iodide (PI) were purchased from Fisher Scientific (USA). CELLTITER-GLO® was purchased from Promega (USA).

1.2 Preparation of PLA-IOC (Iron Oxide Cluster) Films

PLA films, with or without IONPs, were prepared by a one-step spin coating method. The films were prepared on a square cover glass (22 mm×22 mm) that was then placed in the center of the spin coating device. Briefly, IONPs were dispersed in a PLA solution (2%, 4% and 8% (w/v) in chloroform); the concentration of IONPs in the PLA solution varied between 0.01%, 0.1%, and 0.2% (w/v). The IONPs-PLA dispersions were first sonicated for 1 minute with a tip sonicator (Branson digital sonifier, Danbury, USA) at an amplitude of 10%. Next, 0.5 mL of a dispersion was applied onto a cover glass that was then placed in the center of the spin coating device. The speed and time for spin coating was set at respectively 2000 rpm and 20 seconds. After spin coating, the films were placed overnight in an oven at 50° C. to allow evaporation of any residual organic solvent.

To prepare fluorescent PLA-IOC films, PLA (2%, w/v) and Rhodamine B (0.01% w/v) (Sigma-Aldrich, Belgium) were dissolved in chloroform overnight. Then, iron oxide nanoparticles (0.1% w/v) were added to the PLA-Rhodamine B solution. Next PLA-Rhodamine B films were prepared as described in the paragraph above.

1.3 Surface Morphology of PLA-IOC Films

The surface morphology of the PLA-IOC films was characterized by scanning electron microscopy (SEM, FEI Quanta 200F (Thermo Scientific)). The SEM images were acquired with an acceleration voltage of 20 kV. It should be noted that depending on the concentration of the IONPs, iron oxide clusters (IOCs) of different sizes could be observed.

As the iron oxide particles are arranged in clusters of iron oxide particles (IOCs) the films are referred to as PLA-IOC films (instead of PLA-IONP films). The size and the distribution of the IOCs were calculated based on SEM images.

1.4 Laser-Induced Formation of Vapor Bubbles (VNBs) and VNB Threshold

To evaluate whether PLA-IOC films have the ability to generate VNBs, they were irradiated with a pulsed laser (HE 355 LD laser, OPOTEK Inc.; 7 ns, 561 nm). VNBs can be easily visualized by dark-field microscopy as they scatter light during their lifetime. Dark-field images of the films (covered with a thin layer of water) were recorded before and during irradiation of the films with laser pulses with a varying fluence. The "VNB threshold," which is the fluence of a single laser pulse at which 90% of the IOCs form a VNB, was determined by plotting the number of bubbles as a function of the laser fluence.

1.5 Cell Culture

Hela cells (ATCC® CCL-2™) were cultured (at 37° C. and 5% $CO_2$) in DMEM/F-12 (Gibco-Invitrogen) supplemented with 10% fetal bovine serum (FBS, Biowest), 2 mM glutamine and 100 U/mL penicillin/streptomycin (Gibco-Invitrogen). For splitting, cells were first washed with Dulbecco's Phosphate Buffered Saline (DPBS) and then detached using a trypsin-EDTA solution (Gibco-Invitrogen).

For the "cells on top" experiments (FIG. 2) Hela cells were seeded on top of PLA-IOC films present at the bottom of wells in a 6-well plate; the Hela cell concentration was $1 \times 10^6$ cells/mL; in each well 2 mL of cells was applied. After one day of incubation, the PLA-IOC films on which cells adhered were removed from their initial wells and placed into new wells (of a 6-well plate); this to remove the cells that were not in contact with the films but just adhered to plastic bottom of the wells.

For the experiments where the PLA-IOC films were placed on top of the cells ("structure on top of the cells") (FIG. 3), Hela cells were seeded in the wells of a 6-well plate at a concentration of $0.5 \times 10^6$ cells/mL (2 mL). The following day, the Hela cells in the wells were covered with a PLA-IOC film. To maximize the contact between the cells and the film, 90% of the cell medium was removed before applying the film so that only a small layer of medium remained on top of the cells.

1.6 Cell Killing by PLA-IOC Films Exposed to Pulsed Laser Light

Cells were seeded onto a PLA-IOC film or cells were covered with a PLA-IOC film as described above.

The PLA-IOC films were then irradiated with a nanosecond pulsed laser (pulse duration <7 ns, 532 nm wavelength). A galvano scanner was used to allow a fast scanning of the laser beam so that each location essentially received a single laser pulse (or two in the overlapping region between neighboring spots); a single scanning of the whole surface of a PLA-IOC film in a well of a 6-well plate took around 2 minutes. In some cases, the films were scanned multiple times as indicated in the text.

The extent of cell killing by PLA-IOC films exposed to light pulses was evaluated by measuring the metabolic activity of the cells using the CELLTITER-GLO® assay. The assay was performed as recommended by the manufacturer, though with some slight modifications. In brief, following the treatment of the cells on the PLA-IOC films with light pulses, they were placed in a cell incubator for 2 hours to allow sufficient time to die. After 2 hours, the cell medium was removed and replaced by 1 mL of new cell medium (DMEM/F-12) supplemented with 1 mL of CELLTITER-GLO® solution. The well plate was then put on a shaker at 120 rpm for 10 minutes at room temperature. Finally, 150 µL of the supernatant was transferred into the wells of a 96-well plate and the absorbance was measured with a microplate reader (Victor 3, PerkinElmer).

1.7 Measuring the Permeabilization of Cell Membranes

To evaluate to what extent applying laser pulses on the PLA-IOC films permeabilized the membranes of cells, cells were seeded onto a PLA-IOC film or cells were covered with a PLA-IOC film as described above. In case cells were grown on a film, 1 mL DMEM/F-12 cell culture medium containing FITC-dextran (molecular weight 500 kDa; FD500) at a concentration of 2 mg/mL was added. In case a film was applied on top of the cells, 300 µl of DMEM/F-12 cell culture medium containing FD500 (2 mg/ml) was added on the cells before applying the film. The (whole surface of the) films were scanned with the laser beam (as described above; at a fluence of 0.3 J/cm$^2$ or 1.6 J/cm$^2$) and the cells were extensively washed with DPBS for several times to remove the excess of FD500. The cells were then trypsinized (using a 0.25% trypsin solution) and neutralized with cell medium. The suspension of cells was collected and washed by centrifugation for several times (500 g; 5 minutes). Finally, the pellet was resuspended in flow buffer (DPBS, 1% Bovine Serum Albumin (BSA) and 0.1% NaN3). The cytosolic delivery of FD500, which only happens after membrane permeabilization, was measured by flow cytometry (Cytoflex, Beckman Coulter, Krefeld, Germany); the fluorescent dye was excited at 488 nm while the fluorescence intensity was detected at 530 nm (bandpass filter 530/30).

1.8 Spatial Selective Cell Killing by PLA-IOC Films Exposed to Pulsed Laser Light In a first set of experiments, Hela cells were seeded in a 6-well plate on top of PLA-IOC films (0.1% IONPs). Laser pulses, with increasing fluences, were applied on the films, in pre-defined zones. After laser irradiation, the cells on the PLA-IOC films were placed in an incubator (37° C., 5% CO$_2$) for 2 hours. Then 1 µl of calcein AM (0.5 mmol) and 10 µl propidium iodide (1 mg/ml) were added into each well. Calcein AM was used to stain living cells and propidium iodide to stain dead cells. After 10 minutes of incubation, the cells were imaged by confocal microscopy (C1-si, Nikon, Japan). The extent of cell killing in the treated zones was evaluated.

In a second set of experiments, PLA-IOC films (without or with 0.1% of IONPs) were applied on top of Hela cells seeded as described above. Four consecutive laser irradiations at 1.6 J/cm$^2$ were performed according to a pre-defined pattern (similar to logo of Ghent University). After laser scanning, 2 mL DMEM/F-12 was added to the wells and the films were carefully removed from the cells. After 30 minutes, 2 µl calcein AM (0.5 mmol) and 20 µl propidium iodide (1 mg/ml) were added to stain both the living and dead cells.

1.9 Single Cell Killing by PLA-IOC Films Exposed to Pulsed Laser Light

To evaluate to which extent the irradiation of PLA-IOC films with pulsed laser light allows specific killing of a chosen target cell ("single cell killing"), cells were seeded the cells on top of PLA-IOC films as described above. First, the (living) cells were stained by adding 2 µl of calcein AM (0.5 mmol) into each well. A single cell was then randomly selected as the target and imaged by fluorescence microscopy. Subsequently one laser pulse (varying fluence) was applied on the target cell. After 30 minutes, 10 µL propidium iodide (1 mg/ml) was added into each well and cells were imaged again by fluorescence microscopy. The red and green fluorescence of the cells was analyzed using ImageJ software. Cells in the wells were also imaged by transmission microscopy; movies were recorded and processed by ImageJ software.

1.10 Inductively Coupled Plasma Mass Spectrometry (ICP-MS) Measurements

Hela cells were seeded into a 6-well plate as described above. In the absence of laser treatment, either cell culture medium (1.5 ml), a suspension of free IONPs (1.5 ml; 1 g/l) or a PLA-IOC film (keeping of very thin layer of medium between the film and the cells) was added/applied to/on the cells in a well. After 20-minute incubation (37° C., 5% CO$_2$), the cell medium/free IONPs (or the film in the well was/were removed. Then 1.5 mL nitric acid (65%) was added for 10 minutes to each well to digest the cells. After 10 minutes, 1 mL was collected from each well for ICP-MS analysis.

To measure the effect of laser treatment, 20 minutes after applying cell medium/free IONPs/PLA-IOC film (see paragraph above), each well was scanned four times (1.6 J/cm$^2$). After laser treatment, the film was removed and the well was gently washed with fresh cell culture medium twice. Subsequently, 1.5 mL nitric acid (65%) was added to each well for 10 minutes. After digestion of the cells, 1 mL solution was collected from each well for ICP-MS analysis.

(Ultra-)trace element determination of iron (Fe) was carried out using an Agilent 8800 ICP-MS/MS instrument (ICP-QQQ, Agilent Technologies, Japan). The sample introduction system comprises a concentric nebulizer (400 µL min−1) mounted onto a Peltier-cooled (2° C.) Scott-type spray chamber. This instrument is equipped with a tandem mass spectrometry configuration consisting of two quadrupole units (Q1 and Q2) and a collision/reaction cell (CRC) located in-between both quadrupole mass filters (Q1-CRC-Q2). As a result of a much better control over the in-cell chemistry (chemical resolution), the MS/MS mode provides additional means to deal with spectral overlap in a more straightforward way compared to traditional single-quadrupole ICP-MS instrumentation. In this work, the CRC was pressurized with a mixture of NH3/He (10% NH3 in He) to overcome the spectral interferences seriously hampering (ultra-)trace element determination of Fe, such as the overlap between the signals of 40ArO+ and 40CaO+ polyatomic interferences and those of the most abundant Fe isotope (56Fe+, 91.7%) at mass-to-charge—m/z—56. To overcome spectral overlap, 56Fe$^+$ ions were mass-shifted to 56Fe(NH$_3$)$^{2+}$ reaction product ions upon introduction of 3.0 mL min−1 of NH$_3$/He. After mass-shifting, 56Fe$^+$ can be detected free from spectral interferences at the m/z ratio of the newly created reaction product ion (56Fe(NH$_3$)$^{2+}$, m/z=90).

For ICP-MS/MS analysis, only high-purity reagents were used. Ultra-pure water (resistivity 18.2 MΩ cm) was obtained from a Milli-Q Element water purification system (Millipore, France). Pro-analysis purity level 14 M HNO$_3$ (Chem-Lab, Belgium) further purified by sub-boiling distillation and ultra-pure 9.8 M H2O2 (Sigma Aldrich, Belgium) were used for sample digestion. Appropriate dilutions of 1 g L−1 single element standard solutions of Fe and Ga (Inorganic Ventures, USA) were used for method development, optimization and calibration purposes. For quantitative element determination of Fe, external calibration was relied on as calibration approach (0, 0.5, 1.0, 2.5, 5.0, 10 and 20 µg L$^{-1}$ Fe). 5.0 µg L$^{-1}$ of Ga were used as internal standard to correct for instrument instability, signal drift and matrix effects.

Prior to sample preparation for ICP-MS/MS analysis, all samples were transferred from Eppendorf tubes to Teflon Savillex beakers, which had been pre-cleaned with $HNO_3$ and HCl and subsequently rinsed with MILLI-Q® water. After evaporation until dryness (80° C.), the samples were digested via acid digestion with a mixture of 750 μL of 14 M $HNO_3$ and 250 μL of 9.8 M $H_2O_2$ at 110° C. on a hot plate for approximately 18 hours. Prior to ICP-MS/MS analysis, the digested samples were appropriately diluted in MILLI-Q® water or $HNO_3$ (final acid concentration ranging between 0.35 and 0.70 M $HNO_3$). To avoid contamination, only metal-free tubes were used for standard and sample preparation (15 or 50 mL polypropylene centrifuge tubes, VWR, Belgium). The complete sample preparation procedure, including digestion and adequate dilutions, was carried out in a class-10 clean room.

1.11 Killing of Superficial Corneal Cells by PLA-IOC Films Exposed to Pulsed Laser Light Fresh excised bovine eyes were collected from a local slaughterhouse (Flanders Meat Group, Zele). After enucleation, the eyes were maintained in cold $CO_2$ independent medium (Gibco-Invitrogen) during transit and were processed within one hour. The excess of tissue was removed and the eyes were washed in cold DMEM. PLA films (2% PLA) without or with 0.1% IONPs (w/v) were used. The PLA-IOC films were placed into a 55 mm glass bottom dish with a 30 mm micro-well (Cellvis, USA) and filled with 3 mL cell culture medium. Subsequently, the eye was transferred into the dish and fixed with parafilm to immobilize it, making sure that the cornea was in close contact with the PLA-IOC film. To know whether applying laser pulses permeabilized the membranes of the corneal cells, the cell culture medium was supplemented with FD500 (4 mg/mL).

The whole cornea was repeatedly (4 times) scanned with the pulsed laser at a fluence of 1.6 $J/cm^2$. After the irradiation, the eyes were washed three times with DPBS. To assess the killing efficiency, the eyes were placed in a new dish, supplemented with fresh DMEM/F-12 medium containing propidium iodide (0.01 mg/ml) and incubated during 15 minutes at room temperature.

Finally, a 12 mm button was punched into the cornea using a trephine blade (Beaver Visitec International, Abingdon, UK). The thus isolated corneal tissue was placed on a glass bottom dish with the epithelial side down and imaged by confocal microscopy (Nikon A1R). Z-stacks with steps of 1 μm were recorded and 3D images were obtained using available software.

For spatial selective cell killing experiments, the excess of tissue from fresh bovine eyes was removed and eyes were washed in DPBS. A solution of calcein AM (5 μg/ml) was applied at the level of the cornea to stain living epithelial cells and eyes were incubated at room temperature for 10 minutes. The eyes were then washed three times in DPBS and the cornea was isolated using a trephine blade. The corneas were then placed on top of the film PLA-IOC film. Epithelial cells could be observed by fluorescence microscopy and a single cell was targeted before being irradiated with the laser (561 nm; <7 ns).

2. Results 2.1 Physicochemical Characterization of PLA-IOC Films

Figure 5:
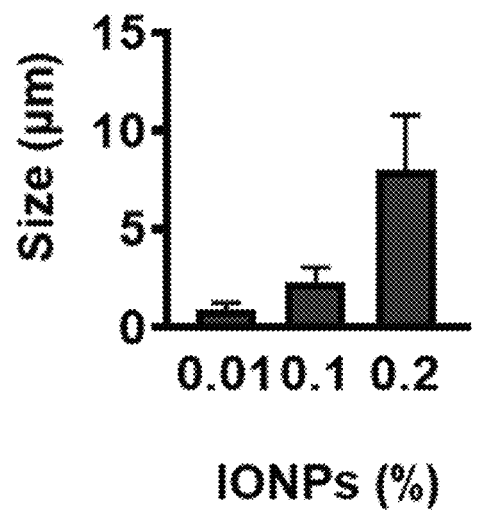
FIG. 5 shows the average size of a cluster of particles in a PLA film in function of the concentration of IONPs.
Figure 6:
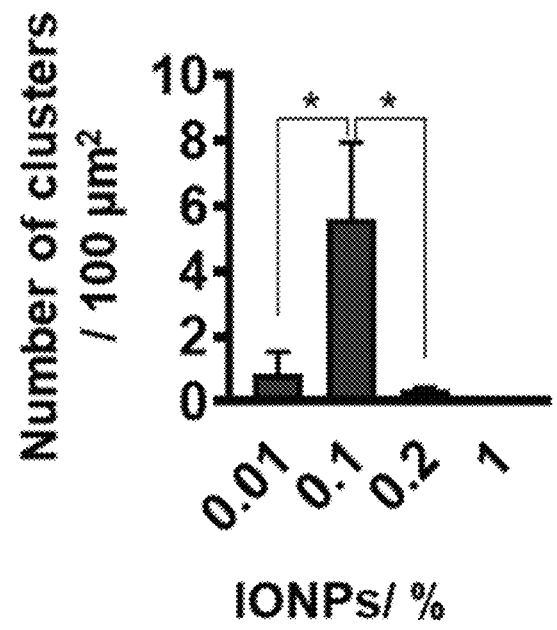
FIG. 6 shows the cluster density (number of clusters of particles/100 µm$^2$) in a PLA film in function of the concentration of IONPs.

To be able to target each single cell in the cell culture (or tissue), ideally each single cell should be in contact with/in close proximity of at least one IOC. A well-controlled distribution of IOCs in the PLA films is therefore requested. SEM-imaging of the PLA-films revealed that IONPs were embedded as clusters (IOCs) within the films; some IOCs were partially protruding out of the films. The average size and the distribution of IOCs in the films depended on the IONP concentration. Indeed, a higher concentration of IONPs (for a fixed concentration of PLA) resulted in larger clusters (FIG. 5). The cluster density equaled 5.6±2.4 IOCs/100 $μm^2$ for a concentration of 0.1% IONPs, while it was lower at a higher IONP concentration (FIG. 6), which can be explained by the formation of larger clusters.

2.2 Laser-Induced Vapor Bubble Formation by PLA-IOC Films

Figure 7:
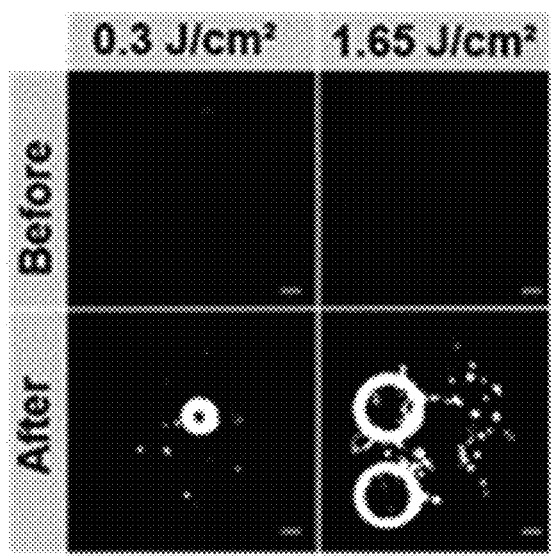
FIG. 7 shows images obtained by dark field microscopy before and after irradiation of a PLA-IOC film (0.1% IONs, 2% PA) with a single laser pulse of respectively 0.3 J/cm$^2$ and 1.6 J/cm$^2$.

To evaluate whether applying pulsed-laser light to PLA-IOC films resulted in the formation of vapor bubbles (VNBs) at the surface of the films, the PLA-IOC films were irradiated with a single laser pulse of respectively 0.3 $J/cm^2$ and 1.6 $J/cm^2$. Irradiation of a PLA-IOC film (0.1% IONs, 2% PA) with such laser pulsed gave rise to VNBs, as localized flashes of (scattered) light were detected by dark field microscopy (FIG. 7). No VNBs could be observed from PLA films without IOCs. At the lower fluence, the number of VNBs was clearly lower than at the higher fluence.

Subsequently, the number of VNBs as a function of the fluence of the laser pulse was measured and the VNB threshold of the PLA-IOC films (0.1% IONPs; 2% PLA), commonly defined as the laser fluence at which 90% (T90) of the IOCs form VNB, was determined to be 0.56 $J/cm^2$. T10, corresponding to the laser fluence at which 10% of the IOCs result in the formation of VNB, was determined to be 0.1 $J/cm^2$. For fluences lower than T10, heat generation is predominant (heating mode); between T10 and T90 both confined heat and bubbles are generated; for fluences higher than T90, VNB formation is the predominant photothermal effect (bubble mode).

For the experiments that follow, PLA films containing 0.01% IONPs were selected. Attractive as well is that such PLA-IOC films are as transparent as PLA films without IOCs.

2.3 Cell Killing by PLA-IOC Films Exposed to Pulsed Laser Light

Figure 8:
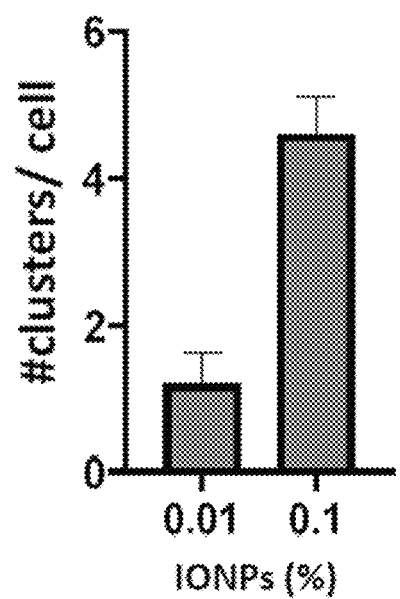
FIG. 8 shows the number of clusters per Hela cell grown on PLA-IOC films having different concentrations of IONP.

Subsequently, the capacity of PLA-IOC films to kill Hela cells that were grown on the surface ("cells on top") of the films (FIG. 2) was evaluated. IOCs in the films could be easily observed as they scatter light strongly (refractive index of iron oxide is 2.9). Based on images of cells grown on the PLA-IOC films, it was estimated that each cell was in contact with 4.6+/−0.5 IOCs (FIG. 8) when the concentration of IONPs in the films equaled 0.1%; at a lower (0.01%) concentration of IONPs, each cell was in contact with 1.2+/−0.4 IOCs.

Figure 9:
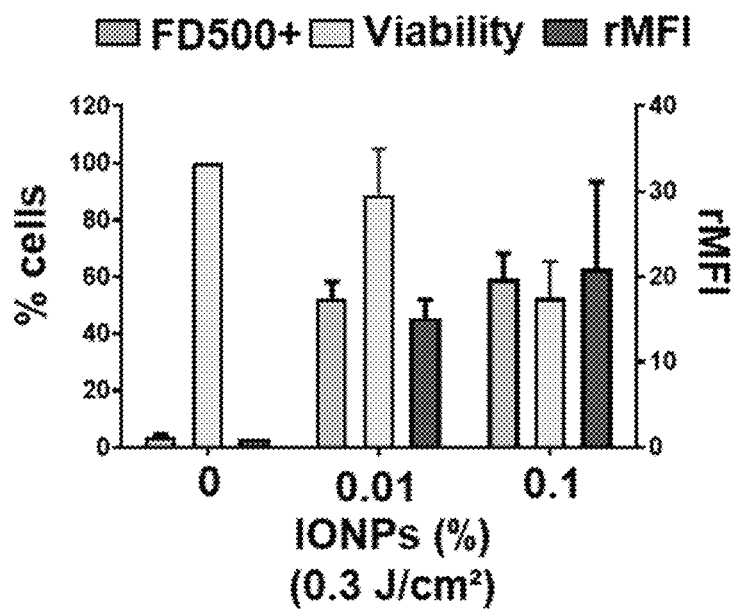
FIG. 9 shows the uptake of FD500, the cell viability and rMFI (relative mean fluorescence intensity) of Hela cells grown on PLA films with 0.1% IONPs.
Figure 10:
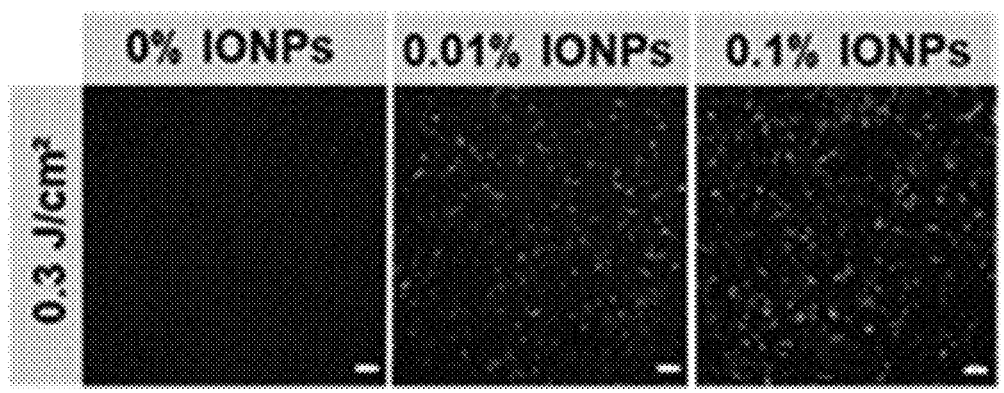
FIG. 10 shows images obtained by confocal microscopy showing the uptake of FD500 grown on PLA films with 0.1% IONPs irradiated with a single laser pulse of 0.3 J/cm$^2$.

FIG. 9 shows that (most) cells grown on PLA-IOC films with 0.01% IONPs survive (as measured by flow cytometry; calcein AM staining) when the films are scanned with a laser at low fluence (single scan; 0.3 $J/cm^2$). With a higher amount of IONPs in the PLA films (0.1%) and at the same fluence, a significant number of cells became killed (cell viability 52.8±12.6%). Also note that all cells grown on a PLA film without IONPs survived the laser treatment. To visualize changes in cell membrane permeability following laser irradiation (which might cause cell killing), fluorescent dextrans (FD500) were added to the cells. Due to their large size (around 30 nm), FD500 do not diffuse over cell membranes and have therefore been reported to be well suited to assess significant permeability changes of plasma membranes. As FIGS. 9 and 10 show, FD500 entered into Hela cells following the irradiation of PLA-IOC films with a laser pulse; note that for PLA-films without IONPs, FD500 did not enter the cells.

Figure 11:
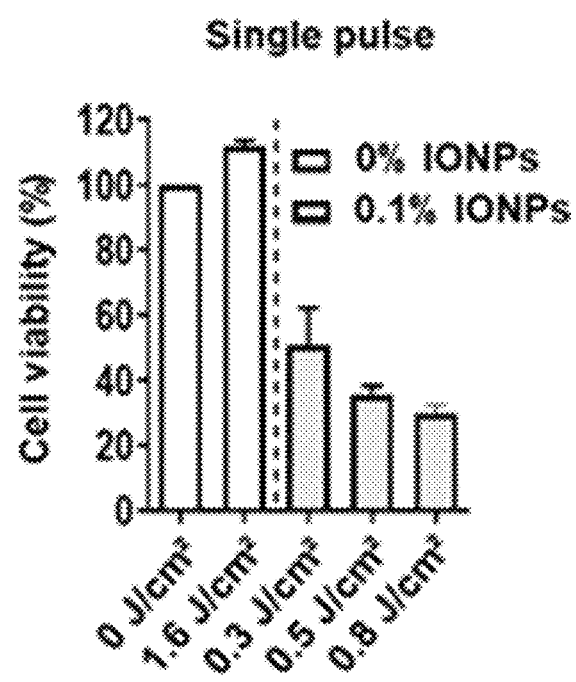
FIG. 11 shows the cell viability of Hela cells grown on PLA-IOC films (without or with 0.1% IONPs) as a function of the laser fluence after a single irradiation.
Figure 12:
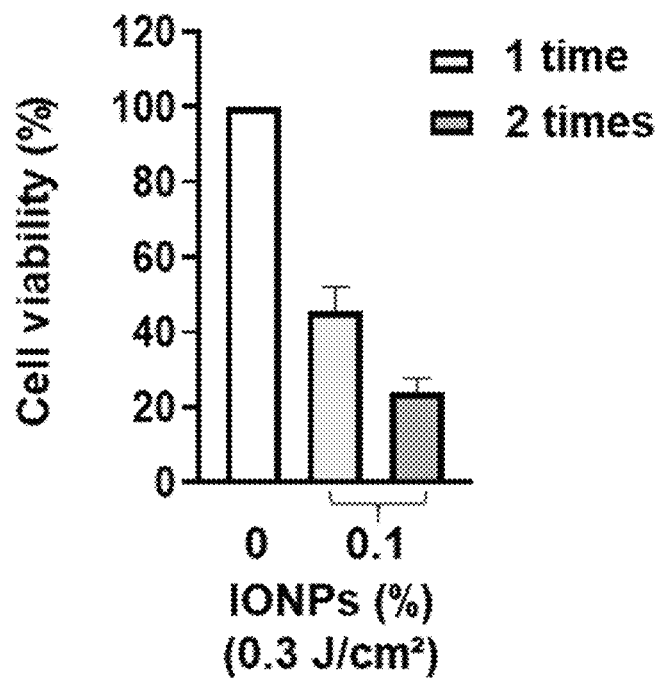
FIG. 12 shows the cell viability of Hela cells grown on PLA-IOC films (0.1% IONPs) irradiated with one or two laser pulses of 0.3 J/cm$^2$.

Subsequently, it was evaluated how the killing of cells could be maximized by using respectively higher laser fluences and repeated laser scanning of the films. As FIG. 11 shows, increasing the laser fluence improved the cell killing capacity of PLA-IOC films: the cell viability dropped to 30% at a laser fluence of 0.8 J/cm$^2$. This was not the case for PLA films without IOCs, which did not induce any cell killing, even not at a very high laser fluence of 1.6 J/cm$^2$. As it was observed that the IOCs survived a single laser pulse (i.e., did not fragment), it was hypothesized that applying a second pulse could further enhance the cell killing capacity of the films. To ensure that an effect of a second pulse could be observed, a (low) fluence of 0.3 J/cm$^2$ was selected as after a single pulse of 0.3 J/cm$^2$ approximately 50% of the cells remained viable. Films were thus scanned for two consecutive times at a fluence of 0.3 J/cm$^2$. As can be seen from FIG. 12, the cell viability dropped from 46%±6% (single scan) to 25%±3% (two consecutive scans).

Figure 13:
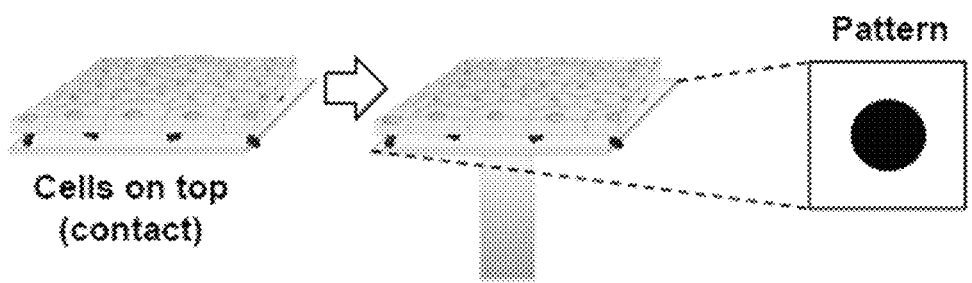
FIG. 13 shows the selective radiation of predefined area (circle with a diameter of 6.5 mm) of a PLA-IOC film (2% PLA, 0.1% IONPs) irradiated with a single pulse at different laser fluences (scale bar is 1000 µm)

2.4 Spatial Selective Cell Ablation and Cell Killing by PLA-IOC Films Exposed to Pulsed Laser Light Given (i) the fact that one can control the density and size of the IOCs in the films and (ii) the inherent ability to scan specific areas in the films, it was evaluated to what extent bubble-films allow to kill target cells with high spatial precision. Therefore, pre-defined circular areas in the PLA-IOC films were scanned with laser pulses with increasing fluences (FIG. 13).

Figure 14:
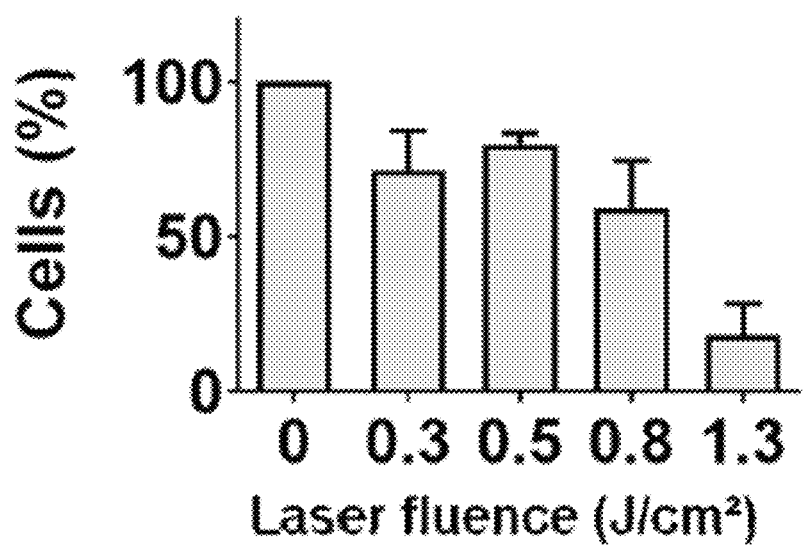
FIG. 14 shows the percentage of retrieved cells after selective radiation as shown in FIG. 13, in function of different laser fluences.
Figure 15:
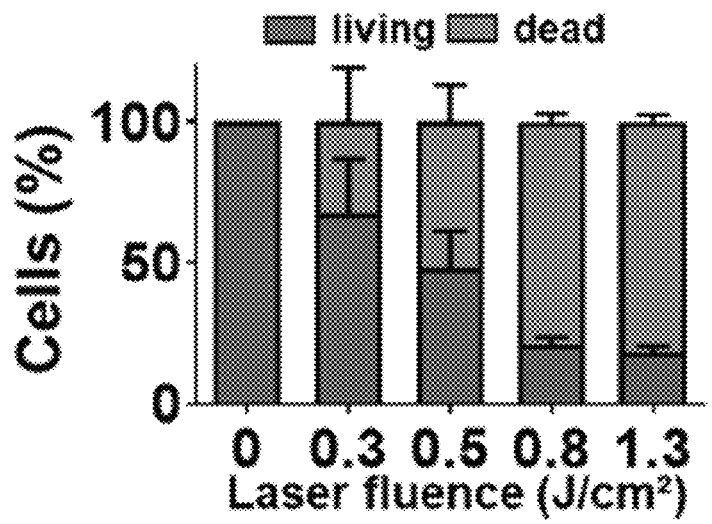
FIG. 15 shows the ratio of living cells (stained with calcein AM) to dead cells (stained with propidium iodide (PI)) after selective radiation as shown in FIG. 13 in function of different laser fluences.

Cells present in the pre-defined areas (circles having a diameter of 6.5 mm) became selectively killed, as could observed by the red fluorescence of propidium iodide (PI) entering dead cells only. It was observed however that at a fluence of 1.3 J/cm$^2$, the total number of cells in the treated areas (living plus dead cells) significantly decreased (FIG. 14), indicating that cells were "lost" (ablated) upon laser treatment, highly likely by the mechanical forces exercised by the vapor bubbles. As shown in FIG. 15, staining the cells with calcein AM and propidium iodide allowed to determine the ratio of living to dead cells remaining in the treated areas; clearly, this ratio gradually dropped upon increasing the laser fluence.

Figure 16:
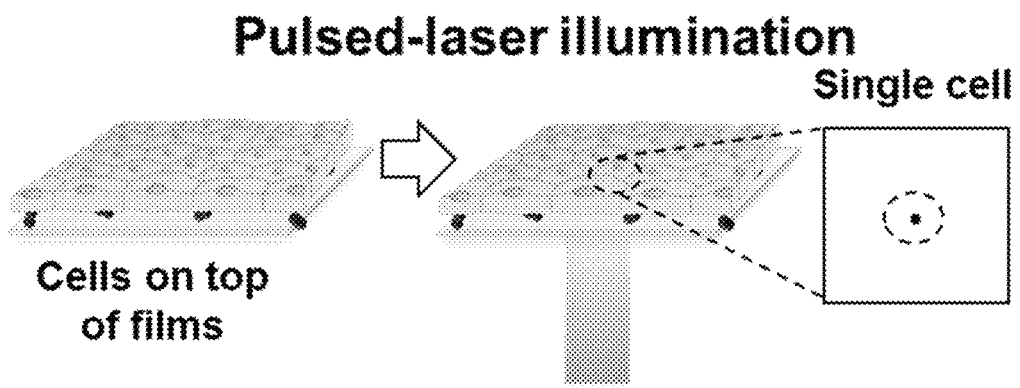
FIG. 16 shows selective cell killing upon local irradiation of a PLA-IOC film (2% PLA, 0.1% IONPs) (scale bar is 10 µm)

FIG. 16 shows single cell killing (the scale bar is 10 μm) upon local irradiation of a PLA-IOC film with a pulsed laser. Single cell killing was obtained, as could observed by the red fluorescence of propidium iodide (PI) entering dead cells only. Transmission images of selective cell treatment of cells on top of films showed single cell ablation at fluences of 1.3 J/cm$^2$. Using a fluence between 0.3 and 0.8 J/cm$^2$ VNBs could be generated though cell ablation did not occur.

Figure 17:
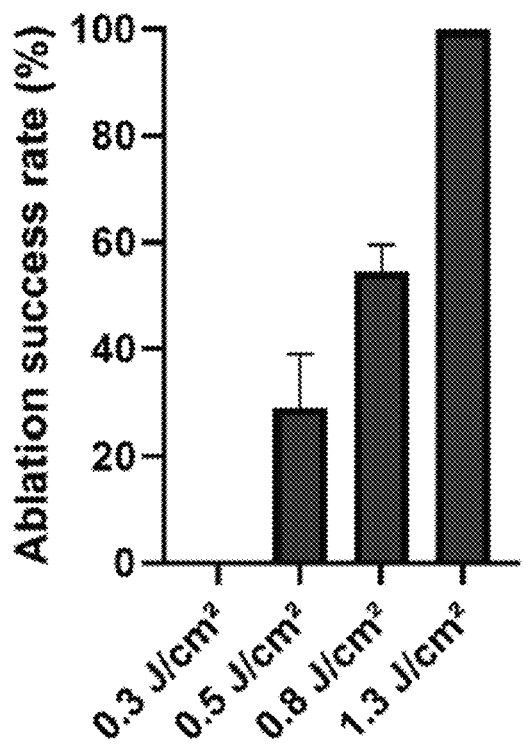
FIG. 17 shows the success rate of single cell ablation for cells grown on PLA-IOC film (2% PLA, 0.1% IONPs) irradiated with a single laser pulse (0.3-1.3 J/cm$^2$). For each value of laser fluence, 30 single cell ablation experiments were done (n=30)

The success rate of single cell ablation increased with the fluence (FIG. 17). Besides, it was observed that while a fluence of 0.3 J/cm$^2$ does not allow single cell ablation, at a fluence of 1.3 J/cm$^2$ single cell ablation was always successful.

Figure 18:
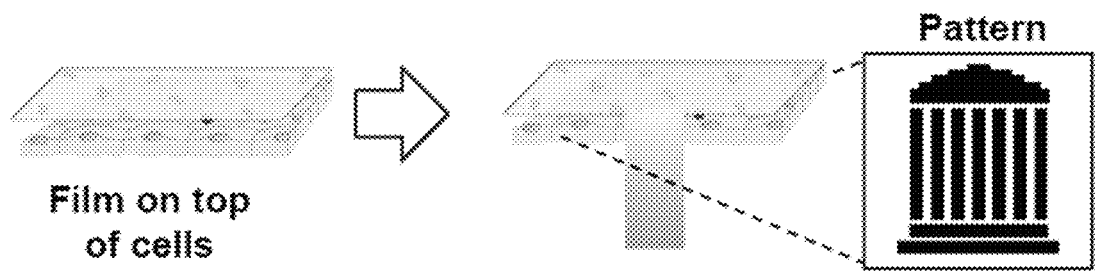
FIG. 18 shows spatial selective laser-induced killing of Hela cells covered with a PLA-IOC film (2% PLA, 0.1% IONPs)

In all experiments above, cells were grown on the PLA-IOC films. To further explore the clinical potential of structures comprising particles according to the disclosure, the cell killing capacity of the films when placed on top of a cell layer (FIG. 18) was evaluated. This mimics the intended use of the films to cover the surface of a target tissue.

Figure 19:
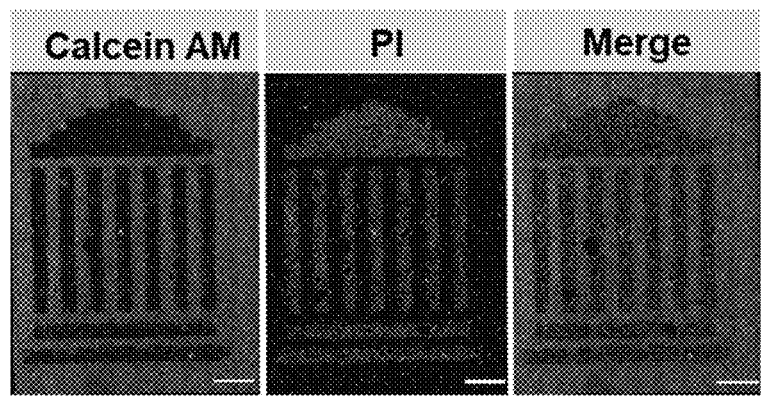
FIG. 19 shows the result of illumination of Hela cells covered with a PLA-IOC (2% PLA, 0.1% IONPs) as shown in FIG. 18, illuminated with a pulsed laser following a pre-defined pattern (Ghent University logo), stained with calcein AM, PI and the merged picture. The scale bar is 1000 µm.
Figure 20:
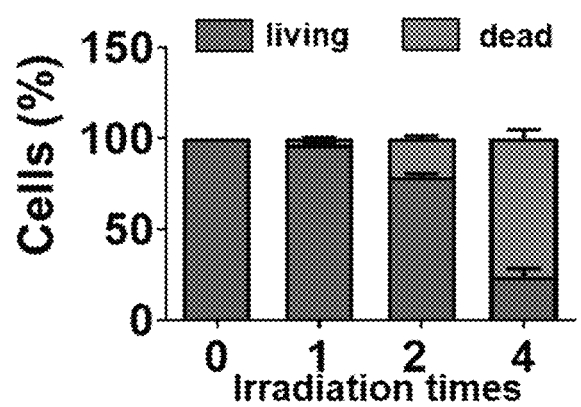
FIGS. 20 and 21 respectively show the ratio of living cells to dead cells and the total amount of cells in the treated area as shown in FIG. 18, following a consecutive number of laser pulses using a laser fluence of 1.6 J/cm$^2$.
Figure 21:
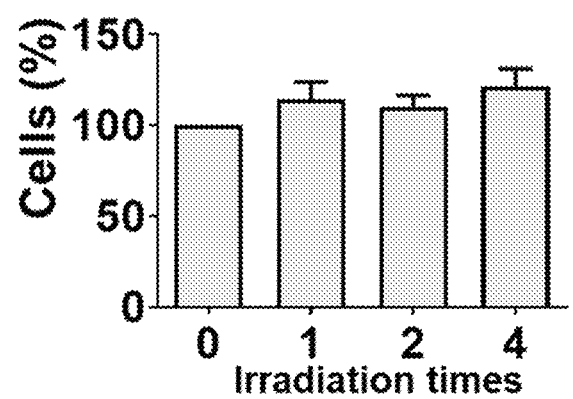

As outlined in the experimental section, after seeding the cells in a 6-well plate the cell medium was removed, though leaving a thin layer of medium on top of cells; subsequently a PLA-IOC film was placed on top of the cells. The distance between the cells and the film was estimated to be 40 μm. A pre-defined area in the film (Ghent University logo) was then exposed to the laser (FIG. 19). As a larger distance between the film and the cells as compared to experiments in FIG. 13 where cells were cultured directly on top of the film was estimated, a higher fluence of 1.6 J/cm$^2$ was used. As FIG. 20 shows, cells became killed, though four pulses were required to realize a ratio of living to dead cells of around 25%. Also note that the total number of cells did not change (FIG. 21), likely because of the longer distance between the cells and the IOCs, lowering the mechanical forces by VNBs acting on the cells.

Figure 22:
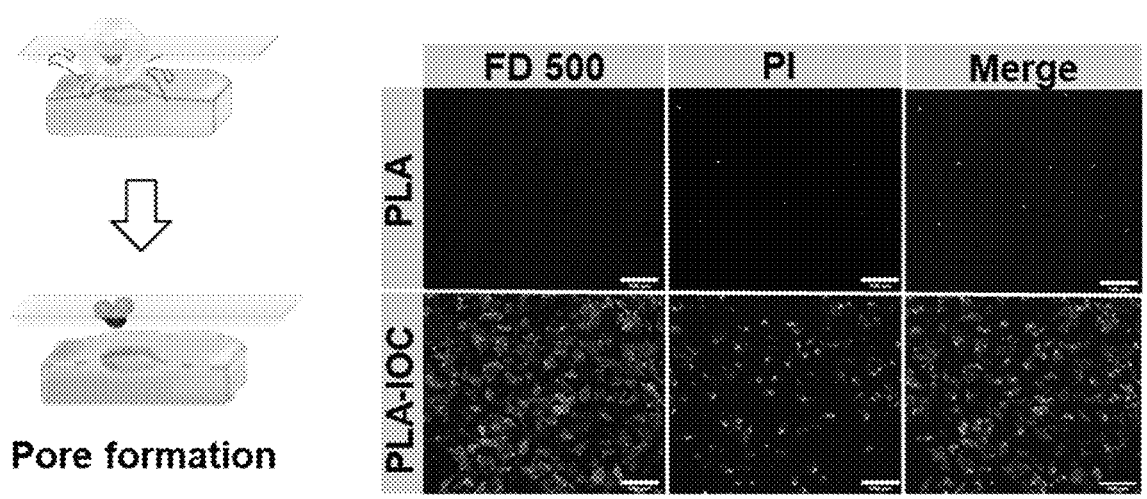
FIG. 22 is a schematic representation of pore formation during cell killing if a PLA-IOC films is positioned on top of the cells (as shown in FIG. 18) (left) and the resulting uptake of FD500 by Hela cell (right) after irradiation (1.6 J/cm², four consecutive times)

To evaluate whether poration of cell membranes is also involved in the killing of the cells if PLA-IOC films are positioned on top of the cells (FIG. 22 (left)), cells were incubated with FD500 and covered with a film. The film was then subsequently irradiated (1.6 J/cm$^2$; four consecutive times). As shown in FIG. 22 (right), green (FD500) and red (PI) fluorescence could be observed in cells, while fluorescence was much lower in cells covered with a PLA film without IOCs and irradiated with laser pulses.

Figure 23:
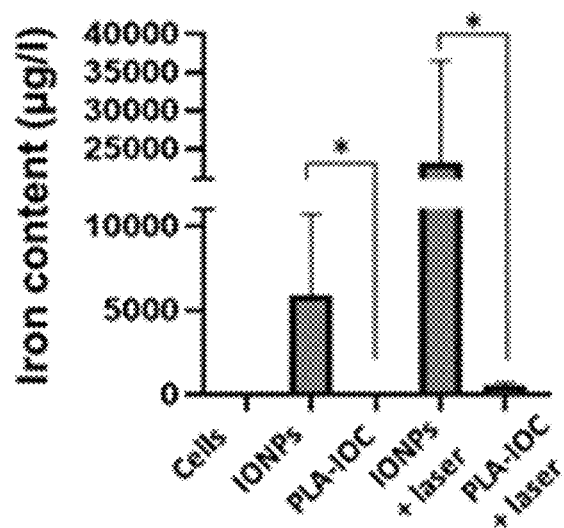
FIG. 23 shows the ICP-MS analysis (iron content) on the Hela cells following four consecutive irradiations (1.6 J/cm²) of the PLA-IOC film; "cells" refer to untreated cells; "IONPs" and "IONPs+laser" refer to cells in the presence of free IONPs (1 g/L), respectively, without or with laser treatment; "PLA-IOC" and "PLA-IOC+laser" concern cells covered with a PLA-IOC film, respectively without and with laser treatment. Data are shown as mean±SD. Statistical significance: Student's t test, *indicates p<0.05, ** indicates p<0.01, ns indicates nonsignificant.

To determine the amount of intracellular iron after laser irradiation of PLA-IOC films covering cells, ICP-MS experiments were performed. As shown in FIG. 23, exposing the cells to free IONPs (1 g/L, being equivalent to the concentration of iron in the films) leads to a higher iron content of the cells. Laser irradiation of the free IONPs further increases the iron levels in the cells. This is likely attributed to (i) the fragmentation of IONPs into smaller fragments and (ii) VNBs (as generated by the free IONPs), which porate cell membranes, thereby facilitating iron uptake. In cells covered with a PLA-IOC film (without laser treatment) the iron content remains as low as in untreated cells. Upon irradiating the PLA-IOC films an increase in intracellular iron content could be observed. However, the intracellular iron content remains far below the amount in cells treated with free IONPs and laser.

Figure 24:
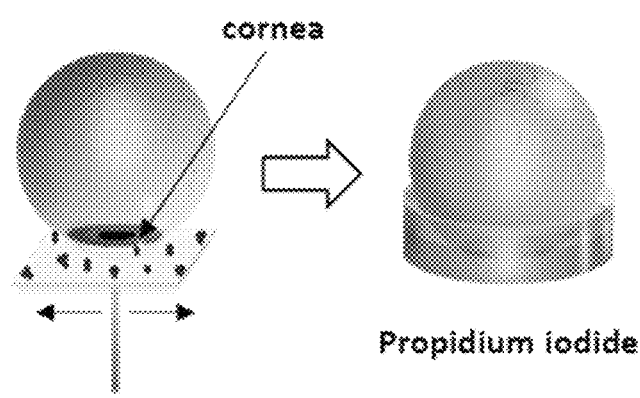
FIG. 24 shows laser-induced killing of cells in bovine cornea covered with a PLA-IOC film (2% PLA, 0.1% IONPs). The corneas were excised and stained with propidium iodide. The whole cornea of the enucleated bovine eye was illuminated four times with a laser pulse of 1.6 J/cm².
Figure 25:
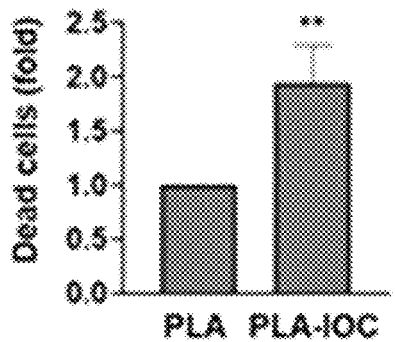
FIG. 25 shows the number of stained cells (dead cells) resulting from the laser-induced killing of cells shown in FIG. 24, using a PLA-IOC film compared to control experiments (PLA film without IOCs)
Figure 26:
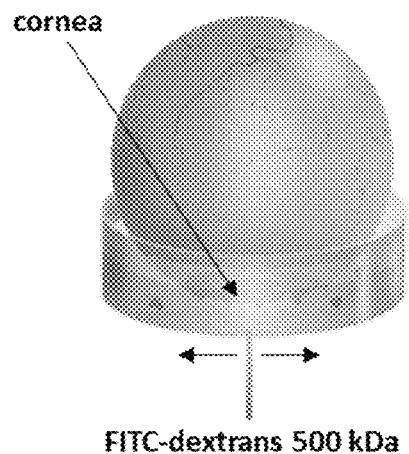
FIG. 26 shows laser-induced killing of cells in bovine cornea covered with a PLA-IOC film (2% PLA, 0.1% IONPs). Corneas were excised and immersed in FD500 solution. IOC film (2% PLA, 0.1% IONPs). The whole cornea of the enucleated bovine eye was illuminated four times with a laser pulse of 1.6 J/cm².
Figure 27:
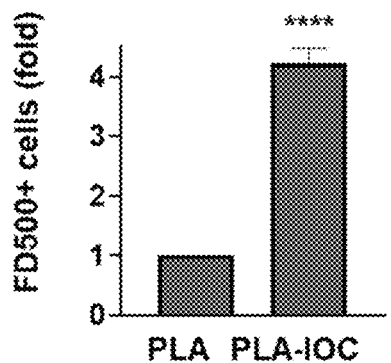
FIG. 27 shows the uptake of FD500 resulting from the laser-induced killing of cells shown in FIG. 26 using a PLA-IOC film compared to control experiments (PLA film without IOCs)

2.5 Killing of Superficial Corneal Cells by PLA-IOC Films Exposed to Pulsed Laser Light As efficient cell killing could be achieved when films were positioned on top of a cultured cell layer (FIG. 18), it was in a next step evaluated whether superficial cells of a tissue (cornea) could be killed by a structure according to the disclosure. As illustrated in FIG. 24, bovine eyes were positioned on the films; the whole cornea was subsequently illuminated four consecutive times at 1.6 J/cm$^2$. Corneas were then excised, stained with PI and imaged by confocal microscopy. The first observation was that, somewhat unexpectedly, PI positive cells were present in the control eyes, i.e., eyes without PLA films or covered with PLA films without IOCs. This is likely because (i) ex vivo bovine corneal epithelial cells already start dying few hours after enucleation and (ii) it is known that epithelial cell death can physiologically occur due to shear forces caused by blinking, for instance. However, confocal microscope images confirmed that a significant increase in PI positive cells was observed in corneas covered with PLA-IOC films irradiated four times with 1.6 J/cm$^2$ laser pulses compared to control experiments using PLA films without IOCs (FIG. 25).

To confirm membrane poration of the corneal cells, the experiments were repeated in the presence of green fluorescent FD500. Confocal microscope images show a clear difference in green fluorescence in corneas covered with PLA-IOC films and treated with four pulses of 1.6 J/cm$^2$ compared to control experiments using PLA films without IOCs. This observation indicates that poration of corneal cell membranes indeed occurred. Important as well is that the green fluorescence (FD500) did not co-localize with the red fluorescence of naturally died cells, indicating that the formation of pores is due to laser irradiation of the PLA-IOC film covering the cornea. It was observed that FD500 did not penetrate untreated corneal cells.

Figure 28:
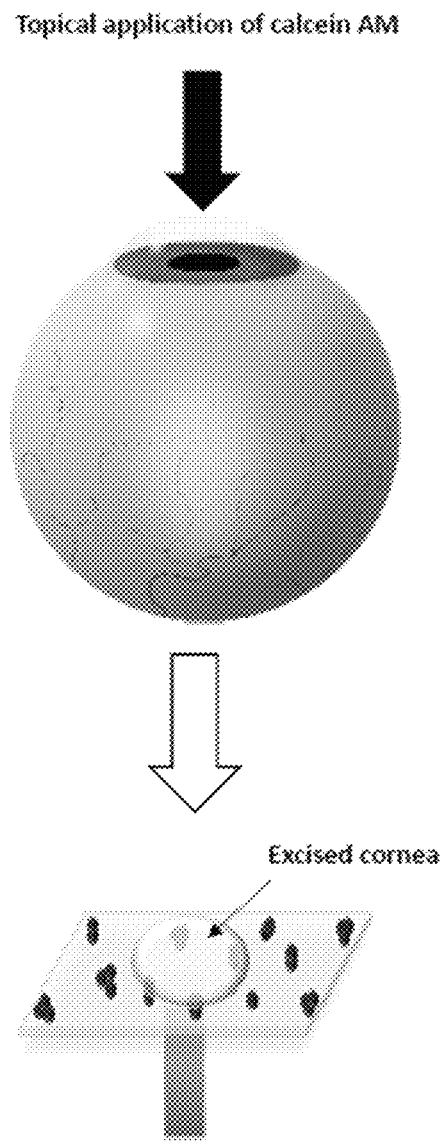
FIG. 28 shows corneal epithelium of bovine eyes stained with calcein, isolated and placed on top of a PLA-IOC film, followed by illumination of a single cell, four times at a fluence of 1.6 J/cm² and 4.5 J/cm².

To check if spatial selective cell killing could be achieved at the level of the cornea, epithelial cells were stained with calcein AM (5 µg/ml). The stained corneas were then placed on top of films (FIG. 28) with the epithelial side down. A region of interest was selected and laser irradiation was applied (<7 ns; 561 nm) four times. After four irradiations at a fluence of 1.6 J/cm$^2$, a local decrease of fluorescence can be observed and irradiated cells lost their staining. At a higher fluence (4.5 J/cm$^2$, four times), cells in the targeted area were not visible anymore suggesting ablation occurs. For both fluences, the surrounding cells (i.e., located outside of the laser beam) did not lose staining after laser irradiation suggesting they were left untouched.

Example 2

A second embodiment of a structure, according to the disclosure, comprises a porous structure comprising nanofibers and particles able to absorb electromagnetic radiation embedded in the nanofibers, whereby a portion of the particles are partially exposed to the free surface S of the structure, in particular, to the free surface of the nanofibers. The below described examples comprise polycaprolactone as material of the structure and iron oxide nanopowder as particles able to absorb electromagnetic radiation. It is clear that other materials and other particles can be considered as well.

1. Materials and Methods 1.1 Materials

The following materials are used for the synthesis of the web of nanofibers:
Polycaprolactone (PCL, Mw≈70,000 g/mol);
N,N-Dimethylformamide (DMF);
Tetrahydrofuran (THF);
iron oxide (Fe$_3$O$_4$) nanopowder (IONP) (#MKBW3262, Sigma-Aldrich, Belgium);
Poly(allylamine hydrochloride) (PAH, Mw=17,560 g/mol, #MKBZ2824V, Sigma-Aldrich, Belgium);
concentrated sulfuric acid solution (96%) (Sigma-Aldrich);
Collagen I Rat Protein (Thermo Fisher Scientific, #A1048301, Gibco™, Belgium).

1.2 Preparation of Structure Comprising Nanofibers and Particles

IONP was re-dispersed in a 1:1 DMF/THE solution to which PCL in different concentrations between 0 vol % and 1.15 vol % was added.

The thus obtained mixture was used to manufacture nanofibers by electrospinning. The nanofibers were collected on microscope glass slides (#1000912, Marienfeld, Germany) mounted on a grounded rotating collector.

IONP was embedded in the nanofibers with a portion of the particles being partially exposed to the free surface S of the nanofibers.

The invention claimed is:

1. An in vitro or ex vivo method to selectively permeabilize and/or fragmentize cells, the method comprising:
providing a structure comprising a material and comprising particles able to absorb electromagnetic radiation, the structure defining a volume V and a free surface S, the free surface S having a free surface area $A_S$, at least a portion of the particles being partially exposed to the free surface S, each of the particles partially exposed to the free surface S defining a particle-free surface P, the particle-free surface P has a particle-free surface area $A_P$, the particles being embedded in the structure in such a way that the sum of the particle-free surface area $A_P$ of all particles ranges between 0.0001% and 50% of the free surface area $A_S$;
providing at least one cell;
bringing the structure and the at least one cell at a distance d less than 100 µm from each other, the distance d being the shortest distance between the at least one cell and the free surface S of the structure; and
irradiating the structure with electromagnetic radiation.

2. The method according to claim 1, wherein at least part of the particles being partially exposed to the free surface S are protruding from the material.

3. The method according to claim 1, wherein the particles have sizes ranging from 1 nm to 40,000 nm.

4. The method according to claim 1, wherein the particles are arranged in clusters with a cluster comprising between 2 and 1,000 particles.

5. The method according to claim 1, wherein the at least one cell comprises a suspension of cells or a tissue of cells.

6. The method according to claim 1, wherein a density of particles being partially exposed to the free surface S of the structure ranges between 1 and 10 particles/100 µm$^2$.

7. The method according to claim 1, wherein the particles comprise particles selected from the group consisting of metal particles, metal oxide particles, carbon or carbon-based particles, particles comprising at least one light-absorbing compound, and particles loaded or functionalized with at least one light-absorbing compound.

8. The method according to claim 1, wherein the material comprises an inorganic material or an inorganic-based material, a ceramic material or a ceramic-based material, an organic material or an organic-based material, a hydrogel or a composite material comprising at least one of these materials.

9. The method according to claim 1, wherein irradiating the structure with electromagnetic radiation comprises irradiating using a pulsed radiation source having pulses with a pulse duration in a range of 1 fs to 1 ms and/or with a fluence per pulse ranging between 0.001 and 10 J/cm$^2$.

10. The method according to claim 1, wherein the structure comprises a film defining a first surface S1 having a first free area surface $A_{S1}$ and a second surface S2, opposite to the first surface S1, having a second free area surface $A_{S2}$, wherein the particles embedded in the structure in such a way that the sum of the particle-free surface area $A_P$ of all particles partially exposed to the first surface S1 ranges between 0.0001% and 50% of the first free area surface $A_{S1}$.

11. The method according to claim 1, wherein the structure comprises a porous structure comprising fibers, particulates, a combination of the fibers and the particulates or a foam, with the particles being embedded in the fibers, the particulates or the foam.

12. A photothermal process to selectively permeabilize and/or fragmentize cells, which photothermal process utilizes a structure, the structure comprising a material and comprising particles able to absorb electromagnetic radiation, the structure comprising a material and comprising particles able to absorb electromagnetic radiation, the structure defining a volume V and a free surface S, the free surface S having a free surface area $A_S$, at least a portion of the particles being partially exposed to the free surface S, each of the particles partially exposed to the free surface S defining a particle-free surface P, the particle-free surface P has a particle-free surface area $A_P$, the particles being embedded in the structure in such a way that the sum of the particle-free surface area $A_P$ of all particles ranges between 0.0001 and 50% of the free surface area $A_S$, the photothermal process comprising:

bringing the structure and the at least one cell at a distance d less than 100 μm from each other, the distance d being the shortest distance between the at least one cell and the free surface area $A_s$ of the structure; and irradiating the structure with electromagnetic radiation to selectively permeabilize and/or fragmentize the at least one cell.

13. The photothermal process according to claim 12, wherein the photothermal process comprises a method of therapy in a subject to selectively permeabilize and/or fragmentize cells of the subject.

14. The photothermal process according to claim 13, wherein the method of therapy comprises nanosurgery.

15. The photothermal process according to claim 12, wherein the at least one cell comprises a suspension of cells or a tissue of cells and/or wherein the electromagnetic radiation comprises pulsed radiation generated by a laser.

* * * * *

UNITED STATES PATENT AND TRADEMARK OFFICE
CERTIFICATE OF CORRECTION

PATENT NO. : 12,091,655 B2
APPLICATION NO. : 18/551165
DATED : September 17, 2024
INVENTOR(S) : Kevin Braeckmans et al.

It is certified that error appears in the above-identified patent and that said Letters Patent is hereby corrected as shown below:

In the Specification

| | | |
|---|---|---|
| Column 2, | Line 67, | change "In case the structure" to --In the case where the structure-- |
| Column 3, | Line 21, | change "disclosure, ranges preferably between" to --disclosure, preferably ranges between-- |
| Column 5, | Line 25, | change "structure ranges preferably between" to --structure preferably ranges between-- |
| Column 5, | Line 27, | change "1 particle/µm$^2$" to --1 particle/100 µm$^2$-- |
| Column 5, | Line 28, | change "2 particles/µm$^2$," to --2 particles/100 µm$^2$,-- |
| Column 5, | Line 28, | change "3 particles/100 µm$^2$ or 4 particles/" to --3 particles/100 µm$^2$, or 4 particles/-- |
| Column 6, | Line 11, | change "In case the particles" to --In the case where the particles-- |
| Column 6, | Line 12, | change "cluster have preferably dimensions" to --cluster preferably have dimensions-- |
| Column 6, | Line 16, | change "A cluster has preferably dimensions" to --A cluster preferably has dimensions-- |
| Column 6, | Line 25, | change "In case a microparticle" to --In the case where a microparticle-- |
| Column 6, | Lines 26-27, | change "such cluster have preferably dimensions" to --such cluster preferably have dimensions-- |
| Column 6, | Lines 33-34, | change "In case a microparticle" to --In the case where a microparticle-- |
| Column 6, | Line 35, | change "such cluster have preferably" to --such cluster preferably have dimensions-- |
| Column 8, | Line 28, | change "In case the structure" to --In the case where the structure-- |
| Column 8, | Lines 28-29, | change "comprises a porous structure the" to --comprises a porous structure, the-- |

Signed and Sealed this
Tenth Day of December, 2024

Katherine Kelly Vidal
*Director of the United States Patent and Trademark Office*

CERTIFICATE OF CORRECTION (continued)
U.S. Pat. No. 12,091,655 B2

|  |  |  |
|---|---|---|
| Column 8, | Line 67, | change "The thickness ranges" to --The thickness preferably ranges-- |
| Column 9, | Line 1, | change "preferably between" to --between-- |
| Column 10, | Line 59, | change "In case the particulates" to --In the case where the particulates-- |
| Column 11, | Lines 25-26, | change "suspension ranges preferably between" to --suspension preferably ranges between-- |
| Column 12, | Lines 17-18, | change "radiation source ranges preferably between" to --radiation source preferably ranges between-- |
| Column 13, | Line 14, | change "one cell comprises preferably a suspension" to --one cell preferably comprises a suspension-- |
| Column 17, | Line 5, | change "free surface area As1 or between" to --free surface area $A_{S1}$ or between-- |
| Column 19, | Line 11, | change "In case cells were" to --In the case where cells were-- |
| Column 19, | Lines 14-15, | change "In case a film was" to --In the case where a film was-- |
| Column 19, | Lines 23-24, | change "and washed by centrifugation for several times" to --and washed several times by centrifugation-- |
| Column 20, | Line 55, | change "from a Milli-Q Element" to --from a MILLI-Q® Element-- |
| Column 21, | Lines 2-3, | change "to Teflon Savillex beakers," to --to TEFLON® Savillex beakers,-- |
| Column 25, | Line 49, | change "a 1:1 DMF/THE solution to" to --a 1:1 DMF/THF solution to-- |

In the Claims

| | | | |
|---|---|---|---|
| Claim 12, | Column 26, | Lines 58-61, | change "structure, the structure comprising a material and comprising particles able to absorb electromagnetic radiation, the structure comprising a material and comprising particles able to absorb electromagnetic radiation, the structure" to --structure, the structure comprising a material and comprising particles able to absorb electromagnetic radiation, the structure-- |